US009643048B1

(12) United States Patent
Danford

(10) Patent No.: US 9,643,048 B1
(45) Date of Patent: May 9, 2017

(54) RESISTANCE BREATHING DEVICE

(71) Applicant: TrainingMask L.L.C., Cadillac, MI (US)

(72) Inventor: Casey Danford, Cadillac, MI (US)

(73) Assignee: TrainingMask L.L.C., Cadillac, MI (US)

( * ) Notice: Subject to any disclaimer, the term of this patent is extended or adjusted under 35 U.S.C. 154(b) by 0 days.

(21) Appl. No.: 15/297,911

(22) Filed: Oct. 19, 2016

Related U.S. Application Data

(60) Provisional application No. 62/385,546, filed on Sep. 9, 2016.

(51) Int. Cl.
A63B 23/18 (2006.01)
A61M 15/00 (2006.01)
(Continued)

(52) U.S. Cl.
CPC .......... A63B 23/18 (2013.01); A61M 16/0683 (2013.01); A61M 16/0866 (2014.02);
(Continued)

(58) Field of Classification Search
CPC .......... A63B 21/00058; A63B 21/0006; A63B 2213/005; A63B 2213/006; A63B 2230/40; A63B 2230/405; A63B 2230/42; A63B 2230/425; A63B 2230/43; A63B 23/18; A63B 23/1859; A62B 9/02; A62B 9/022;
(Continued)

(56) References Cited

U.S. PATENT DOCUMENTS 938,247 A 10/1909 Kuhn
2,406,888 A 9/1946 Meidenbauer, Jr.
(Continued)

FOREIGN PATENT DOCUMENTS

CN 1311705 A 9/2001
CN 3416108 12/2004
(Continued)

OTHER PUBLICATIONS

International Search Report and Written Opinion dated Dec. 7, 2015, issued in International (PCT) Patent Application No. PCT/US2015/051364, filed Sep. 22, 2015 (15 pages).
(Continued)

Primary Examiner — Joshua Lee
(74) Attorney, Agent, or Firm — Greenberg Traurig, LLP

(57) ABSTRACT

A resistance breathing device includes a face mask having a perimeter and an aperture extending therethrough, and being adapted to overlay a user's mouth and nose such that the perimeter forms an air-tight seal with the user's face. An insert is disposed within the aperture of the face mask and has an inlet aperture extending therethrough. An adjustment slide is positioned adjacent the insert, has an inlet aperture extending therethrough, and is movable between a first position in which a first portion of the inlet aperture overlaps the inlet aperture of the insert and a second position in which a larger second portion of the inlet aperture overlaps the inlet aperture of the insert. An adjustment wheel is attached to the insert and is movable rotatably between first and second positions to cause the adjustment slide to move between its first and second positions.

20 Claims, 11 Drawing Sheets

(51) Int. Cl.

| | | |
|---|---|---|
| *A61M 16/00* | (2006.01) | |
| *A62B 7/00* | (2006.01) | |
| *A62B 9/00* | (2006.01) | |
| *A62B 18/00* | (2006.01) | |
| *A62B 18/10* | (2006.01) | |
| *A61M 16/06* | (2006.01) | |
| *A61M 16/20* | (2006.01) | |
| *A61M 16/08* | (2006.01) | |
| *A63B 21/00* | (2006.01) | |
| *A62B 18/02* | (2006.01) | |
| *A62B 9/02* | (2006.01) | |

(52) U.S. Cl.
CPC .......... *A61M 16/208* (2013.01); *A61M 16/20* (2013.01); *A62B 9/02* (2013.01); *A62B 18/02* (2013.01); *A62B 18/10* (2013.01); *A63B 21/00058* (2013.01); *A63B 21/00069* (2013.01)

(58) Field of Classification Search
CPC ......... A62B 9/025; A62B 9/027; A62B 18/00; A62B 18/02; A62B 18/025; A62B 18/08; A62B 18/10; A61M 16/06; A61M 16/0683; A61M 16/08; A61M 16/0866; A61M 16/20; A61M 16/201; A61M 16/204; A61M 16/208; A61M 16/209
See application file for complete search history.

(56) References Cited

U.S. PATENT DOCUMENTS

| | | | |
|---|---|---|---|
| 3,097,642 A | 7/1963 | Russell | |
| 3,633,575 A | 1/1972 | Brumfield | |
| 3,850,171 A | 11/1974 | Ball et al. | |
| 4,064,876 A | 12/1977 | Mulchi | |
| 4,221,381 A * | 9/1980 | Ericson .................. A63B 23/18 | |
| | | | 482/13 |
| 4,300,240 A | 11/1981 | Edwards | |
| 4,549,543 A | 10/1985 | Moon | |
| 4,601,465 A | 7/1986 | Roy | |
| 4,739,987 A * | 4/1988 | Nicholson .............. A63B 23/18 | |
| | | | 128/207.16 |
| 4,770,413 A | 9/1988 | Green | |
| 4,823,828 A * | 4/1989 | McGinnis ............ A61M 16/208 | |
| | | | 128/205.24 |
| 4,961,420 A | 10/1990 | Cappa et al. | |
| 4,973,047 A | 11/1990 | Norell | |
| 5,117,821 A | 6/1992 | White | |
| 5,167,819 A | 12/1992 | Iana et al. | |
| D340,317 S | 10/1993 | Cole | |
| D369,442 S | 4/1996 | Jones | |
| D380,545 S | 7/1997 | Nozaki et al. | |
| 5,649,533 A | 7/1997 | Oren | |
| 5,697,105 A | 12/1997 | White | |
| 5,799,652 A | 9/1998 | Kotliar | |
| 5,848,589 A | 12/1998 | Welnetz | |
| 5,850,833 A | 12/1998 | Kotliar | |
| 5,884,336 A | 3/1999 | Stout | |
| 5,924,419 A | 7/1999 | Kotliar | |
| 5,964,222 A | 10/1999 | Kotliar | |
| 6,006,748 A | 12/1999 | Hollis | |
| 6,070,578 A | 6/2000 | Baughman et al. | |
| D434,879 S | 12/2000 | Cole | |
| D440,302 S | 4/2001 | Wolfe | |
| 6,390,094 B1 | 5/2002 | Slionski | |
| 6,471,621 B2 | 10/2002 | Horstel et al. | |
| 6,508,850 B1 | 1/2003 | Kotliar | |
| 6,554,746 B1 | 4/2003 | McConnell et al. | |
| 6,606,751 B1 | 8/2003 | Kalhok et al. | |
| 6,644,308 B2 | 11/2003 | Kalhok et al. | |
| 6,986,745 B2 | 1/2006 | Farr et al. | |
| 7,523,755 B2 | 4/2009 | Richardson et al. | |
| D636,128 S | 4/2011 | Hancock et al. | |
| 7,931,733 B2 | 4/2011 | Kotliar | |
| D645,956 S | 9/2011 | Grimsley | |
| D666,364 S | 8/2012 | Votel et al. | |
| D670,037 S | 10/2012 | Chen | |
| 8,365,734 B1 | 2/2013 | Lehman | |
| D681,192 S | 4/2013 | D'Souza et al. | |
| D681,881 S | 5/2013 | Pong | |
| 8,443,806 B2 | 5/2013 | Morelli et al. | |
| 8,590,533 B2 | 11/2013 | Danford | |
| D694,875 S | 12/2013 | D'Souza et al. | |
| 8,678,005 B2 | 3/2014 | Dawson | |
| 8,695,599 B2 | 4/2014 | Friberg et al. | |
| 8,746,249 B2 * | 6/2014 | Matula, Jr. ............ A61M 16/06 | |
| | | | 128/205.25 |
| 9,067,086 B2 | 6/2015 | Danford | |
| 9,333,318 B2 * | 5/2016 | Cragg ............... A61M 16/0057 | |
| D765,237 S | 8/2016 | Danford | |
| D767,754 S | 9/2016 | Danford | |
| 9,517,315 B2 * | 12/2016 | Meyer ............... A61M 16/0057 | |
| 2001/0007651 A1 | 7/2001 | Fust | |
| 2001/0029750 A1 | 10/2001 | Kotliar | |
| 2002/0023762 A1 | 2/2002 | Kotliar | |
| 2002/0100893 A1 | 8/2002 | Shultz | |
| 2002/0162556 A1 | 11/2002 | Smith et al. | |
| 2003/0005934 A1 | 1/2003 | Japuntich et al. | |
| 2003/0154984 A1 | 8/2003 | Fernandes | |
| 2004/0118405 A1 | 6/2004 | Amante et al. | |
| 2004/0146842 A1 | 7/2004 | Carlucci et al. | |
| 2004/0226563 A1 | 11/2004 | Xu et al. | |
| 2005/0172968 A1 | 8/2005 | Hishida | |
| 2006/0201431 A1 | 9/2006 | Peterson | |
| 2008/0092898 A1 | 4/2008 | Schneider et al. | |
| 2008/0178884 A1 | 7/2008 | Gerson et al. | |
| 2008/0202774 A1 | 8/2008 | Kotliar | |
| 2008/0210240 A1 | 9/2008 | Kotliar | |
| 2009/0239711 A1 * | 9/2009 | Foley .................. A63B 21/0085 | |
| | | | 482/13 |
| 2009/0320848 A1 | 12/2009 | Steindorf et al. | |
| 2010/0024826 A1 | 2/2010 | Sullivan, Jr. | |
| 2010/0101584 A1 | 4/2010 | Bledstein et al. | |
| 2011/0203593 A1 | 8/2011 | Ishigami et al. | |
| 2011/0212811 A1 | 9/2011 | Rutten | |
| 2012/0080035 A1 * | 4/2012 | Guney .................. A61M 16/06 | |
| | | | 128/205.25 |
| 2012/0094806 A1 | 4/2012 | Danford | |
| 2012/0103339 A1 | 5/2012 | Koehler | |
| 2012/0167891 A1 | 7/2012 | Smaller | |
| 2012/0180800 A1 | 7/2012 | Shibata et al. | |
| 2012/0247474 A1 | 10/2012 | Torbenson | |
| 2013/0060157 A1 | 3/2013 | Beard | |
| 2013/0190643 A1 | 7/2013 | Brambilla | |
| 2013/0319420 A1 * | 12/2013 | Danford .................. A62B 18/10 | |
| | | | 128/206.21 |
| 2014/0202469 A1 | 7/2014 | Smaller | |
| 2014/0224261 A1 | 8/2014 | Tsuei | |
| 2014/0251332 A1 | 9/2014 | Martin | |
| 2014/0261428 A1 | 9/2014 | Chen | |
| 2015/0040907 A1 | 2/2015 | Hakim et al. | |
| 2015/0053206 A1 | 2/2015 | Seppälä | |
| 2015/0173436 A1 | 6/2015 | Tsuei | |
| 2015/0231443 A1 | 8/2015 | Halliday | |
| 2016/0089553 A1 | 3/2016 | Dickstein et al. | |
| 2016/0129286 A1 * | 5/2016 | Danford .................. A62B 18/02 | |
| | | | 128/206.21 |
| 2016/0129287 A1 | 5/2016 | Danford | |
| 2016/0331917 A1 * | 11/2016 | Bennett .................. A63B 23/18 | |

FOREIGN PATENT DOCUMENTS

| | | |
|---|---|---|
| CN | 3525464 | 4/2006 |
| CN | 3611368 | 2/2007 |
| CN | 3627174 | 3/2007 |
| CN | 3638368 A | 4/2007 |
| CN | 3650368 A | 5/2007 |
| CN | 300733965 | 1/2008 |
| CN | 300798841 S | 7/2008 |
| CN | 300853751 S | 11/2008 |
| CN | 301345091 S | 9/2010 |
| CN | 301345092 S | 9/2010 |

(56) References Cited

FOREIGN PATENT DOCUMENTS

| | | |
|---|---|---|
| CN | 102421485 A | 4/2012 |
| CN | 302364261 S | 3/2013 |
| CN | 302560932 S | 9/2013 |
| CN | 302675138 A | 12/2013 |
| CN | 302675148 S | 12/2013 |
| CN | 203523849 U | 4/2014 |
| CN | 302827495 S | 5/2014 |
| CN | 302857904 S | 6/2014 |
| CN | 302857912 S | 6/2014 |
| CN | 302919473 S | 8/2014 |
| CN | 302945765 S | 9/2014 |
| CN | 303061361 S | 12/2014 |
| CN | 104705842 A | 6/2015 |
| CN | 303234768 A | 6/2015 |
| CN | 303312122 S | 7/2015 |
| CN | 303342066 A | 8/2015 |
| CN | 303380407 A | 9/2015 |
| CN | 303405719 A | 10/2015 |
| CN | 303425634 A | 10/2015 |
| EM | 000590377-0004 A | 11/2007 |
| EM | 003165265-001 | 1/2016 |
| EM | 003165265-002 | 1/2016 |
| EP | 2425875 A1 | 3/2012 |
| GB | 5001809 | 2/2016 |
| JP | D2004-19667 | 4/2005 |
| JP | 2010-42087 A | 2/2010 |
| JP | D2010-021935 | 7/2011 |
| KR | 30-0514514 | 12/2008 |
| KR | 30-2008-0014298 | 4/2009 |
| KR | 20-2010-0004312 U | 4/2010 |
| KR | 30-0586700 | 1/2011 |
| KR | 30-0778665 | 1/2015 |
| WO | 00/04957 A1 | 2/2000 |
| WO | 2010/127161 A2 | 11/2010 |
| WO | 2010/127161 A3 | 11/2010 |
| WO | DM082862 | 2/2014 |
| WO | 2014059389 A1 | 4/2014 |

OTHER PUBLICATIONS

U.S. Appl. No. 14/951,837, filed Nov. 25, 2015, entitled "Resistance and Filtration Breathing Device" (42 pages).
Office Action for Applicant's related Japan Design Application No. 2016-001555, mailed Jul. 5, 2016 by the Japanese Patent Office, and English-language translation thereof (4 pages).
ReBNA product catalogue published by Patent Works, Inc., obtained by the Japan National Center for Industrial Property Information and Training on Mar. 21, 2008 (1 page).
Design Patent Right Evaluation Report completed Jul. 4, 2016, issued by the State Intellectual Property Office of China in Applicant's related China Design Patent No. ZL201530482604.X and English-language translation thereof (18 pages).
Design Patent Right Evaluation Reported completed Jul. 4, 2016, issued by the State Intellectual Property Office of China in Applicant's related China Design Patent No. ZL201530482542.2 and English-language translation thereof (23 pages).
International Search Report and Written Opinion of the International Searching Authority, mailed Aug. 8, 2016, issued by the European Patent Office in Applicant's related International Application No. PCT/US20151064042 (11 pages).
Design Patent Right Evaluation Report dated Mar. 21, 2016, issued by the State Intellectual Property Office of China in Patent No. ZL201530349470.4 and English-language translation thereof (31 pages).
Patentability Assessment Report, completed Jul. 20, 2016, issued by the State Intellectual Property Office of China in Applicant's related China Utility Patent No. ZL2015208912778 and English-language translation thereof (15 pages).
Printouts of Phantom Athletics website http://www.phantom-trainingmask.com/en/ advertising a resistance breathing levice, accessed Jan. 26, 2016 (8 pages).
Photographs of a resistance breathing device, purchased Jun. 3, 2016, along with redacted invoice for such purchase (9 pages).
Printouts of Phantom Athletics website, archived by Archive.org, available at https://web.archive.org/web/20160129132023/http://www.phantom-trainingmask.com/en/phantom-trainingmask.com/en/phantom-trainingmask, accessed Sep. 1, 2016.
U.S. Appl. No. 29/556,825, filed Mar. 3, 2016, entitled "Resistance Breathing Device" (6 pages).
U.S. Appl. No. 14/989,400, filed Jan. 6, 2016, entitled "Resistance Breathing Device" (43 pages).
Design Patent Right Evaluation Report dated Aug. 10, 2016, issued by the State Intellectual Property Office of China in Patent No. ZL201630018279.6 and English-language translation thereof (27 pages).
2015 Under Armour Future Show, Oct. 13, 2015, available at Http://www.youtube.com/watch?v=-EyX1AtkGls, accessed Jan. 11, 2017.
Do Elevation Masks Work?, Ciaran Fairman, available at Http://www.bodybuilding.com/content/do-elevation-masksovork.html, accessed Jan. 11, 2017.
Training Mask 2.0 Instructional Video With Warm Up, Jul. 24, 2014, available at Https://www.youtube.com/watch?v=uw1i9S9iHLg, accessed Jan. 11, 2017.
International Search Report and Written Opinion of the International Searching Authority, mailed Nov. 22, 2016, issued by the European Patent Office in Applicant's related International Application No. PCT/US20161024498 (13 pages).
Office Action issued by the U.S. Patent and Trademark Office on May 6, 2016 in Applicant's U.S. Appl. No. 14/989,400 for "Resistance Breathing Device", filed Jan. 6, 2016.
Office Action issued by the U.S. Patent and Trademark Office on Dec. 2, 2016 in Applicant's in Applicant's U.S. Appl. No. 14/536,794 for "Scent Suppression Mask", filed Nov. 10, 2014.
Office Action issued by the U.S. Patent and Trademark Office on Aug. 9, 2016 in Applicant's U.S. Appl. No. 14/951,837 for "Resistance and Filtration Breathing Device", filed Nov. 25, 2015.
U.S. Pat. No. 29/579,559, filed Sep. 30, 2016, entitled "Resistance Breathing Device" (7 pages).

* cited by examiner

RESISTANCE BREATHING DEVICE

CROSS-REFERENCE TO RELATED APPLICATION

This application is a Section 111(a) application relating to and claiming the benefit of commonly owned, U.S. Provisional Patent Application No. 62/385,546, titled "RESISTANCE BREATHING DEVICE," having a filing date of Sep. 9, 2016, which is incorporated by reference herein in its entirety.

FIELD OF THE INVENTION

The present invention relates to wearable breathing devices. More particularly, the present invention relates to wearable breathing devices providing resistance to air inhalation.

BACKGROUND OF THE INVENTION

Individuals who are training for physical fitness or athletic competition may wish to improve the efficiency of their cardiovascular systems for improved health and stamina. More particularly, individuals may wish to condition their cardiovascular systems by performing training or exercise activities while restricting their ability to inhale air and oxygen.

SUMMARY OF THE INVENTION

In an embodiment, a resistance breathing device includes a face mask, an outer layer, an insert, an adjustment slide, an adjustment wheel, and an air exhaust valve assembly. The face mask has an interior surface, an exterior surface opposite the interior surface, an aperture extending through the face mask from the exterior surface to the interior surface, and a perimeter. The face mask is adapted to overlay a user's mouth and nose such that the perimeter forms an air-tight seal with the user's face and around the user's mouth and nose and the face mask defines an internal area between the interior surface of the face mask and the user's face. The outer layer overlays the face mask and has a pair of straps with inter-engaging ends for affixing the face mask about the user's face. The insert has an interior surface, an exterior surface opposite the interior surface of the insert, and at least one inlet aperture extending therethrough. The insert is positioned within the aperture of the face mask. The adjustment slide has an interior surface, an exterior surface opposite the interior surface of the adjustment slide, and at least one inlet aperture extending therethrough. The adjustment slide is positioned adjacent to the insert such that the interior surface of the adjustment slide abuts the exterior surface of the insert. The adjustment slide is movable linearly along a linear axis with respect to the insert between a first position and a second position. When the adjustment slide is in its first position, a first portion of the at least one inlet aperture of the adjustment slide overlays a first portion of the at least one inlet aperture of the insert. When the adjustment slide is in its second position, a second portion of the at least one inlet aperture of the adjustment slide overlays a second portion of the at least one inlet aperture of the insert. The second portion of the at least one inlet aperture of the adjustment slide is larger in size than the first portion of the at least one inlet aperture of the adjustment slide. The adjustment wheel is attached movably to the insert such that the adjustment wheel is movable rotatably with respect to the insert between a first position and a second position. The first position of the adjustment wheel corresponds to the first position of the adjustment slide. The second position of the adjustment wheel corresponds to the second position of the adjustment slide. When the adjustment wheel is moved between its first position and its second position, the adjustment slide is moved between its first position and its second position. The air exhaust valve assembly is adapted to prevent air from passing therethrough from an external environment to the internal area and is adapted to allow air to pass therethrough from the internal area of the face mask to the external environment.

In an embodiment, the adjustment slide includes a first plurality of teeth, the adjustment wheel includes a second plurality of teeth, and the adjustment slide and the adjustment wheel are positioned adjacent one another such that the first plurality of teeth of the adjustment slide mesh with the second plurality of teeth of the adjustment wheel. In an embodiment, the adjustment wheel rotates about a rotational axis to move between its first position and its second position. The rotational axis is perpendicular to the linear axis.

In an embodiment, the resistance breathing device also includes a retainer having an interior surface, an exterior surface opposite the interior surface of the retainer, and at least one inlet aperture. The retainer overlays the adjustment slide such that the interior surface of the retainer abuts the exterior surface of the adjustment slide so as to maintain the adjustment slide in its position adjacent the insert and such that the at least one inlet aperture of the retainer overlays the at least one inlet aperture of the insert. In an embodiment, the adjustment slide includes a plurality of grooves formed in the exterior surface of the adjustment slide and spaced along the linear axis, the retainer includes a ridge projecting from the interior surface of the retainer, the ridge of the retainer is positioned within a first one of the plurality of grooves of the adjustment slide when the adjustment slide is in its first position, and the ridge of the retainer is positioned within a second one of the plurality of grooves of the adjustment slide when the adjustment slide is in its second position. In an embodiment, the ridge of the retainer is positioned adjacent to the at least one inlet aperture of the retainer. In an embodiment, the ridge of the retainer and the plurality of grooves of the adjustment slide are sized and shaped such that when the ridge is positioned within one of the plurality of grooves, said ridge and the one of the plurality of grooves cooperate to resist movement of the adjustment slide along the linear axis. In an embodiment, the at least one inlet aperture of the retainer is substantially rectangular in shape.

In an embodiment, the at least one inlet aperture of the adjustment slide is substantially rectangular in shape. In an embodiment, the at least one inlet aperture of the adjustment slide has rounded corners. In an embodiment, the at least one inlet aperture of the insert is substantially rectangular in shape. In an embodiment, a size of the at least one inlet aperture of the adjustment slide is equal to a size of the at least one inlet aperture of the insert. In an embodiment, the at least one inlet aperture of the insert is right trapezoidal in shape. In an embodiment, the right trapezoidal shape includes rounded corners. In an embodiment, the at least one inlet aperture of the insert is smaller than the at least one inlet aperture of the adjustment slide.

In an embodiment, the insert includes a first lateral side, a second lateral side opposite the first lateral side, a first side bracket extending from the exterior surface of the insert proximate the first lateral side, and a second side bracket extending from the exterior surface of the insert proximate the second lateral side. The first and second side brackets cooperate to define an allowable range of travel of the adjustment slide along the linear axis. In an embodiment, the resistance breathing device also includes a face plate having an interior surface and an exterior surface opposite the interior surface of the face plate. The face plate overlays the insert and is oriented such that the interior surface of the face plate faces the insert. In an embodiment, the face mask is overmolded to the insert.

In an embodiment, the insert includes at least one outlet aperture positioned offset from the at least one inlet aperture of the insert. Each of the at least one outlet aperture includes a biasing member extending across the one of at least one outlet aperture of the insert and a stem extending from a center of the biasing member and away from the insert. The stem includes a first portion adjacent the center of the biasing member and a second portion opposite the first portion of the stem. The first portion of the stem has a first diameter. The second portion of the stem having a second diameter that is larger than the first diameter. In an embodiment, the air exhaust valve assembly includes the at least one outlet aperture of the insert and at least one flexible membrane. The at least one flexible membrane has a first side, a second side opposite the first side, a profile complementary to the at least one outlet aperture of the insert, a post extending from the first side, and a central hole extending through the post and the first and second sides and sized and shaped to receive the first portion of the stem of the insert. The at least one flexible membrane is disposed adjacent the insert such that the first portion of the stem of each of the at least one outlet aperture of the insert is disposed within the central hole of a corresponding one of the at least one flexible membrane, such that the second side of each of the at least one flexible membrane abuts the biasing member of the corresponding one of the at least one outlet aperture of the insert, and such that the second portion of the stem of each of the at least one outlet aperture abuts the post of the corresponding one of the at least one flexible membrane so as to retain the at least one flexible membrane adjacent to the insert.

BRIEF DESCRIPTION OF THE DRAWINGS

Reference is made to the following detailed description of the exemplary embodiment considered in conjunction with the accompanying drawings, in which.

DETAILED DESCRIPTION OF THE EXEMPLARY EMBODIMENTS

Figure 1:
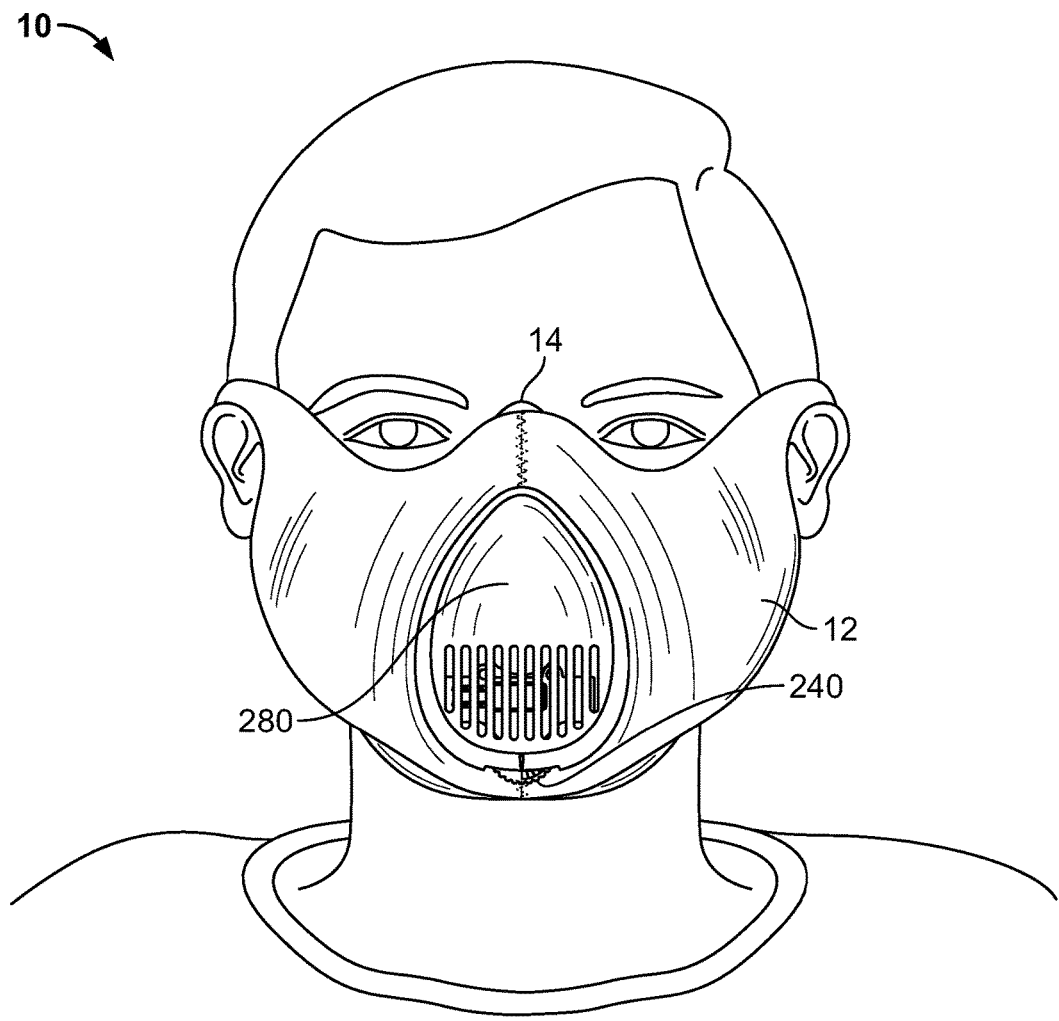
FIG. 1 is a front elevational view of a resistance breathing device in accordance with an exemplary embodiment of the present invention, said device being shown as worn by a user.
Figure 2:
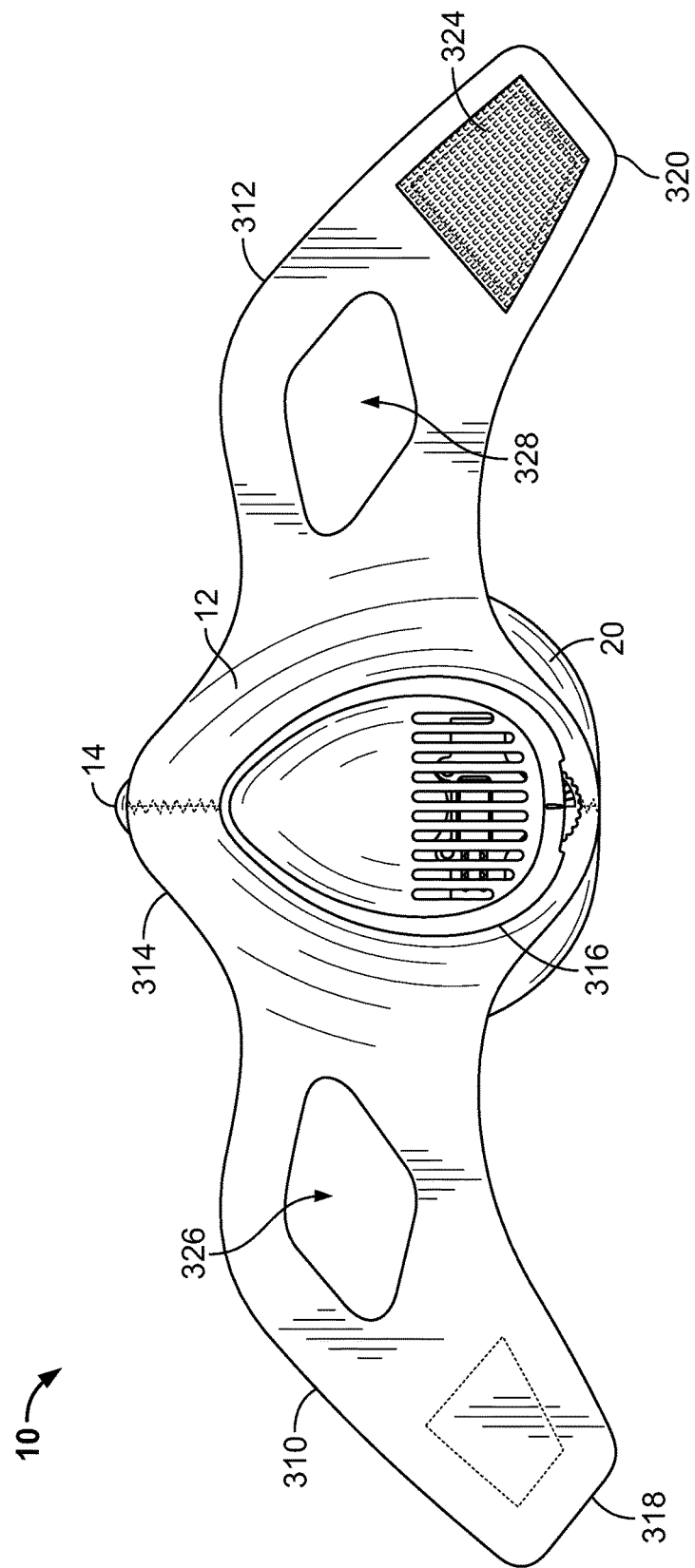
FIG. 2 is a front perspective view of the resistance breathing device shown in FIG. 1, but said device being shown as detached from the user.
Figure 3:
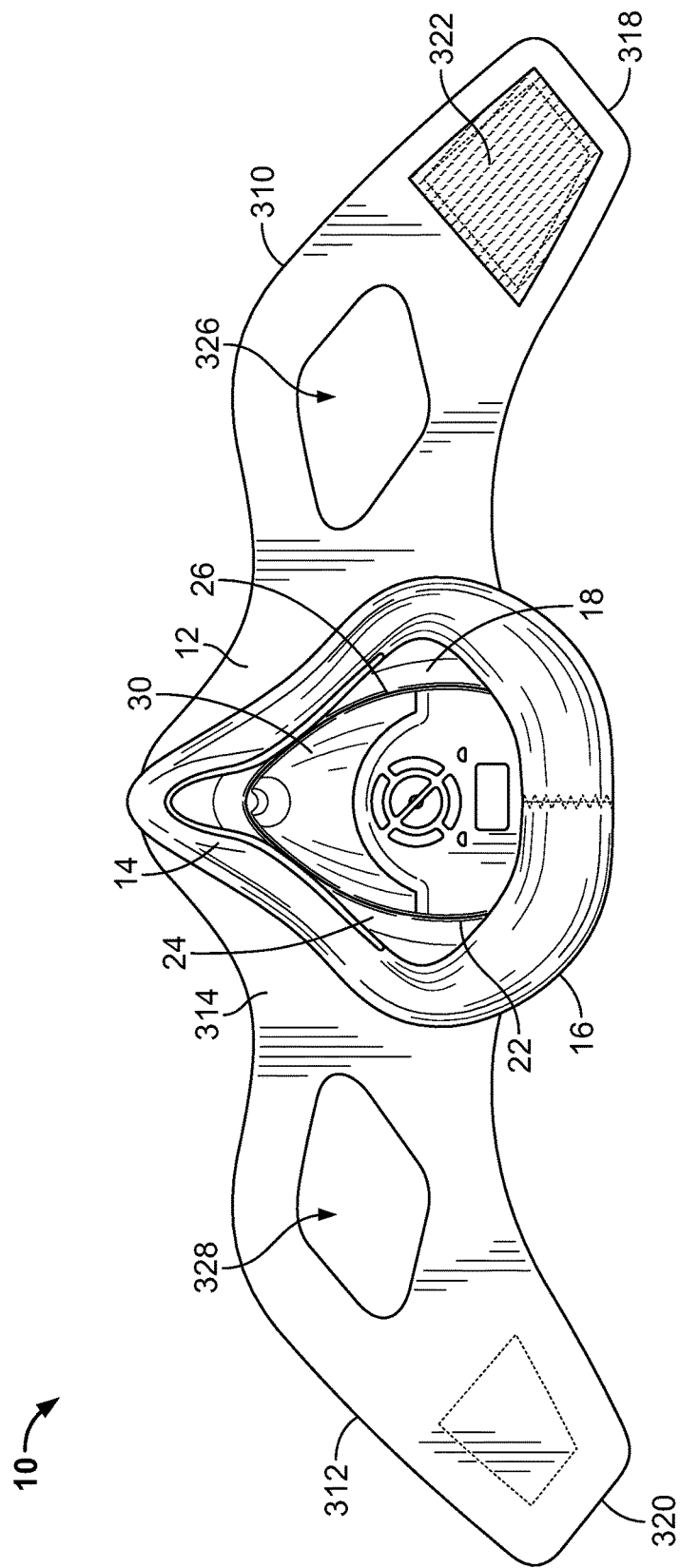
FIG. 3 is a rear perspective view of the resistance breathing device shown in FIG. 2.

FIGS. 1-5C illustrate an exemplary resistance breathing device 10 (hereinafter "device 10"). In an embodiment, the device 10 includes an outer layer 12 overlaying a centrally-located, air-impermeable face mask 14. In an embodiment, the face mask 14 is sized, shaped, and adapted to overlay the nose and mouth of a user. In an embodiment, the face mask 14 includes a perimeter 16 (as shown in FIG. 3) that is adapted to provide an air-tight seal with a user's face. In an embodiment, the face mask 14 is made from rubber. In an embodiment, the face mask 14 is made from a thermoplastic elastomer ("TPE"). In an embodiment, the face mask 14 is made from a TPE distributed by Teknor Apex Company of Pawtucket, R.I. under the trademark MONPRENE. In an embodiment, the face mask 14 is made from silicone. In an embodiment, the face mask 14 is made from styrene-ethylene/propylene-styrene ("SEPS"). In an embodiment, the face mask 14 is made from styrene-ethylene/butylene-styrene ("SEBS"). In an embodiment, the face mask 14 is made from another suitable material known in the art selected such that the perimeter 16 provides an air-tight seal with a user's face.

Referring now to FIGS. 2 and 3, in an embodiment, the face mask 14 includes an interior surface 18 and an exterior surface 20, a substantial portion of which is covered by the outer layer 12. Referring now to FIG. 3, in an embodiment, the face mask 14 includes an aperture 22 extending from the interior surface 18 to the exterior surface 20. In an embodiment, the aperture 22 is encircled by a lip 24. In an embodiment, the lip 24 includes a groove 26 formed therein and extending about the entirety thereof.

Figure 4A:
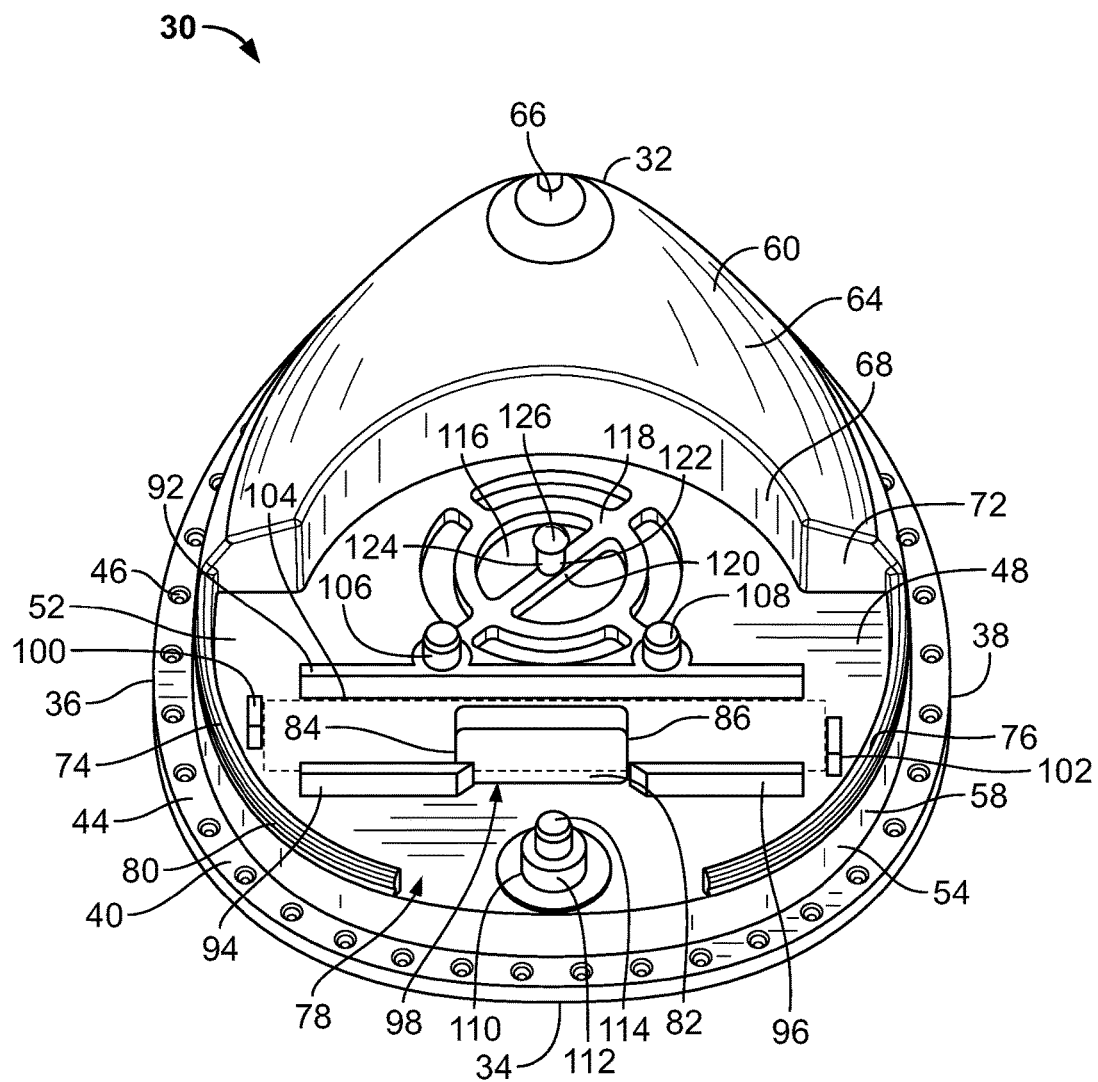
FIG. 4A is a front perspective view of a first embodiment of an insert of the resistance breathing device shown in FIG. 2.
Figure 4B:
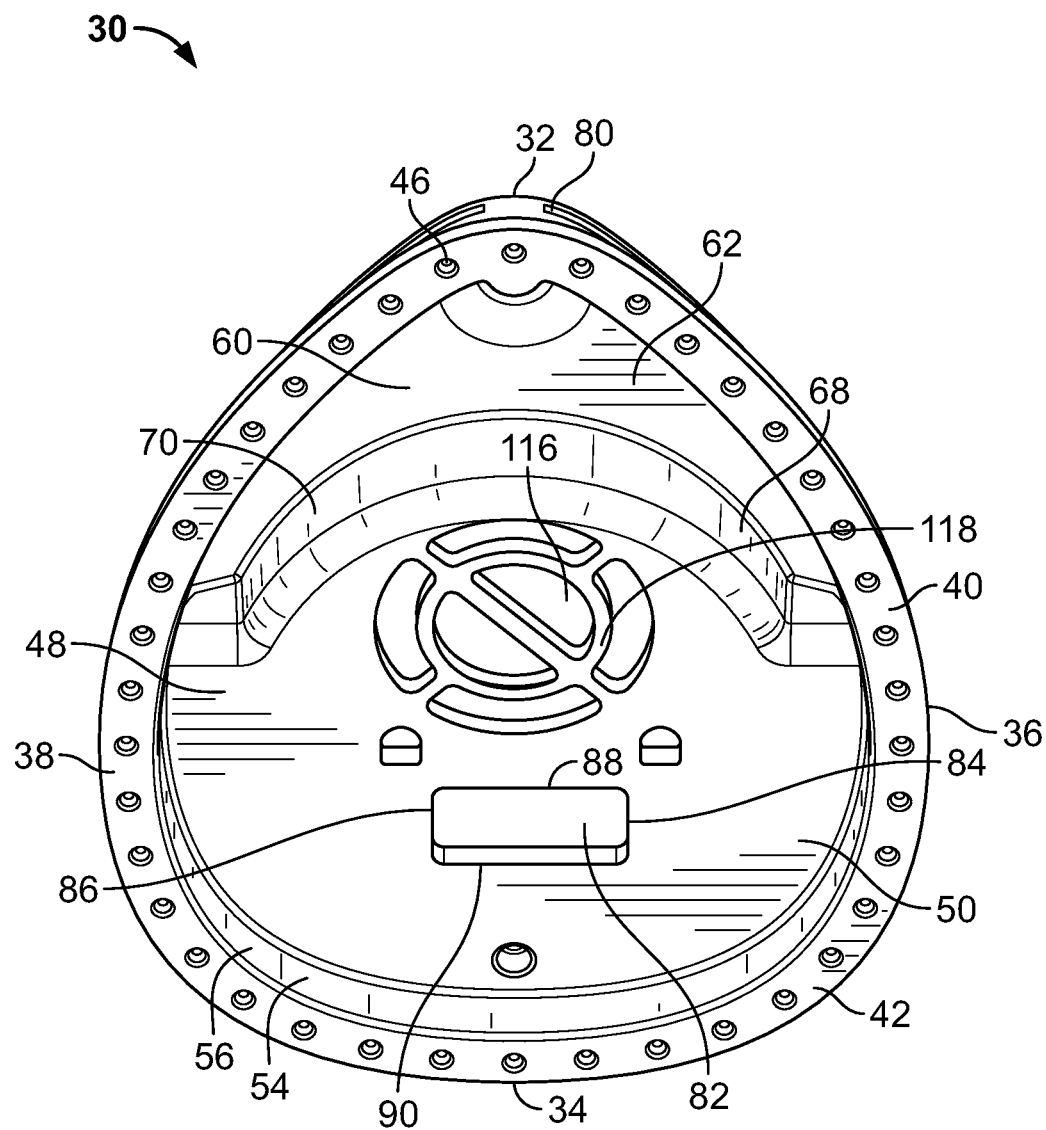
FIG. 4B is a rear perspective view of the insert of FIG. 4A.

Referring now to FIGS. 4A and 4B, in an embodiment, the device 10 includes an insert that is sized and shaped to be retained within the aperture 22 of the face mask 14. In an embodiment, the insert 30 has a profile similar to a rounded triangle. In an embodiment, the insert 30 has a profile similar to a teardrop. In an embodiment, the insert 30 has a profile similar to that of a region overlaying a person's nose and mouth. The insert 30 includes an upper end 32, a lower end 34 opposite the upper end 32, a first lateral side 36, and a second lateral side 38 opposite the first lateral side 36. An outer portion 40 is sized and shaped to be complementary to the aperture 22 of the face mask 14, and extends around the profile of the insert 30. The outer portion 40 is substantially planar and includes an interior surface 42 and an exterior surface 44 opposite the interior surface 42. In an embodiment, an array of perforations 46 extend through the outer portion 40.

Continuing to refer to FIGS. 4A and 4B, the insert 30 includes an inner portion 48 disposed within the outer portion 40. The inner portion 48 is substantially planar and is located in a plane substantially parallel to that of the outer portion 40, but offset from that of the outer portion 40 in a direction away from the exterior surface 44 of the outer portion 40. The inner portion 48 includes an interior surface 50 and an exterior surface 52 opposite the interior surface 50. A first transition portion 54 is formed between the outer portion 40 and the inner portion 48, and includes an interior surface 56 and an exterior surface 58 opposite the interior surface 56.

Continuing to refer to FIGS. 4A and 4B, the insert 30 includes a seating portion 60 that extends from a location proximate the upper end 32 of the insert 30 to a location proximate the first and second lateral sides 36, 38 of the insert 30. The seating portion 60 is offset from the inner portion 48 in a direction away from the exterior surface 52 of the inner portion 48. The seating portion 60 includes an interior surface 62 and an exterior surface 64 opposite the interior surface 62. The seating portion 60 is contoured in a manner such the interior surface 62 is concave and the exterior surface 64 is convex. An indentation 66 is formed within the exterior surface 64 of the seating portion 60 at a location proximate the upper end 32 of the insert 30. A second transition portion 68 is formed between the inner portion 48 and the seating portion 60, and includes an interior surface 70 and an exterior surface 72 opposite the interior surface 70.

Continuing to refer to FIGS. 4A and 4B, the insert 30 includes first and second perimeter portions 74, 76, which protrude from the inner portion 48 in a direction away from the exterior surface 52 of the inner portion 48. The first perimeter portion 74 extends from the second transition portion 68 at a location proximate the first lateral side 36 of the insert 30, and runs in a direction toward, but does not reach, the lower end 34 of the insert 30. The second perimeter portion 76 extends from the second transition portion 68 at a location proximate the second lateral side 38 of the insert 30, and runs in a direction toward, but does not reach, the lower end 34 of the insert 30. A space 78 is formed between the first and second perimeter portions 74, 76.

Continuing to refer to FIGS. 4A and 4B, the insert 30 includes a groove 80 extending about substantially the entire perimeter thereof. The groove 80 is formed at a location proximate the exterior surface 52 of the inner portion 48. The groove 80 begins at the intersection of the first perimeter portion 74 and the space 78 between the first and second perimeter portions 74, 76, and extends around the perimeter of the insert 30, passing the first lateral side 36, the upper end 32, and the second lateral side 38, before ending at the intersection of the second perimeter portion 76 and the space 78 between the first and second perimeter portions 74, 76. In an embodiment, the indentation 66 of the seating portion 60 interrupts the groove 80.

Continuing to refer to FIGS. 4A and 4B, the insert 30 includes an inlet aperture 82 extending through and substantially centered with respect to the inner portion 48. In an embodiment, the inlet aperture 82 has a substantially rectangular shape. In an embodiment, the inlet aperture 82 has a substantially rectangular shape with rounded corners. In an embodiment, the inlet aperture 82 has a first end 84 that is closest to the first lateral side 36 of the insert 30, a second end 86 that is closest to the second lateral side 38 of the insert 30, a first side 88 that is closest to the upper end 32 of the insert 30, and a second side GO that is closest to the lower end 34 of the insert 30. In an embodiment, a width of the inlet aperture 82 from the first end 84 to the second end 86 is greater than a height of the inlet aperture 82 from the first side 88 to the second side 90.

Continuing to refer to FIGS. 4A and 4B, the insert 30 also includes an upper bracket 92 protruding from the exterior surface 52 of the inner portion 48. The upper bracket 92 extends in a direction across the insert 30 from the first lateral side 36 toward the second lateral side 38. The upper bracket 92 is offset from the inlet aperture 82 in a direction toward the upper end 32 of the insert 30.

Continuing to refer to FIGS. 4A and 4B, the insert 30 includes first and second lower brackets 94, 96 protruding from the exterior surface 52 of the inner portion 48. Each of the lower brackets 94, 96 extends in a direction across the insert 30 from the first lateral side 36 toward the second lateral side 38. Each of the lower brackets 94, 96 is offset from the inlet aperture 82 by the same distance in a direction toward the lower end 34 of the insert 30. The first lower bracket 94 extends from a location proximate the intersection of the first end 84 and the second side 90 of the inlet aperture 82, and in a direction toward the first lateral side 36 of the insert 30. The second lower bracket 96 extends from a location proximate the intersection of the second end 86 and the second side 90 of the inlet aperture 82, and in a direction toward the second lateral side 38 of the insert 30. A space 98 is formed between the first and second lower brackets 94, 96.

Continuing to refer to FIGS. 4A and 4B, the insert 30 also includes first and second side brackets 100, 102 protruding from the exterior surface 52 of the inner portion 48. Each of the first and second side brackets 100, 102 extends in a direction from the first end 32 toward the second end 34. The first side bracket 100 is offset from the inlet aperture 82 in a direction toward the first lateral side 36 of the insert 30. The second side bracket 102 is offset from the inlet aperture 82 in a direction toward the second lateral side 38 of the insert 30.

Continuing to refer to FIGS. 4A and 4B, the upper bracket 92, the lower brackets 94, 96, and the side brackets 100, 102 (collectively "the brackets") cooperate to define a rectangle 104 having a width (i.e., as measured between the first side bracket 100 and the second side bracket 102) that is greater than its height (i.e., as measured between the upper bracket 92 and either of the lower brackets 94, 96). It will be apparent to those of skill in the art that the rectangle 104 is an imaginary construct defined herein for descriptive purposes, and not a physical element of the insert 30.

Continuing to refer to FIGS. 4A and 4B, the insert 30 includes first, second, and third posts 106, 108, 110. The first and second posts 106, 108 protrude from the upper bracket 92 in a direction away from the exterior surface 52 of the inner portion 48 of the insert 30, and are located at opposite sides of the inlet aperture 82. In an embodiment, the first and second posts 106, 108 protrude from bases projecting away from the upper bracket 92 in a direction toward the upper end 32 of the insert 30. The third post 110 protrudes from the exterior surface 52 of the inner portion 48 of the insert 30, and is substantially centered within the space 98 between the first and second lower brackets 94, 96. In an embodiment, the third post 110 includes a lower portion 112 having a first diameter and an upper portion 114 having a second diameter that is less than the first diameter. In an embodiment, the diameter of the upper portion 114 of the third post 110, the diameter of the first post 106, and the diameter of the second post 108 are substantially equal to one another.

Continuing to refer to FIGS. 4A and 4B, the insert 30 includes an exhaust aperture 116 extending through the inner portion 48. In an embodiment, the exhaust aperture 116 is offset from said inlet aperture 82, and is located intermediate the upper bracket 92 and the seating portion 60. In an embodiment, the exhaust aperture 116 is circular. In an embodiment, a biasing element 118 extends across the exhaust aperture 116. In an embodiment, the biasing element 118 includes a center 120. In an embodiment, a stem 122 extends from the center 120 of the biasing element 118 in a direction perpendicularly and outwardly from the exterior surface 52 of the inner portion 48. In an embodiment, the stem 122 includes a first portion 124 adjacent to the exterior surface 52 of the inner portion 48 and a free second portion 126 opposite the first portion 124. In an embodiment, a diameter of the first portion 124 is less than a diameter of the second portion 126.

Figure 4C:
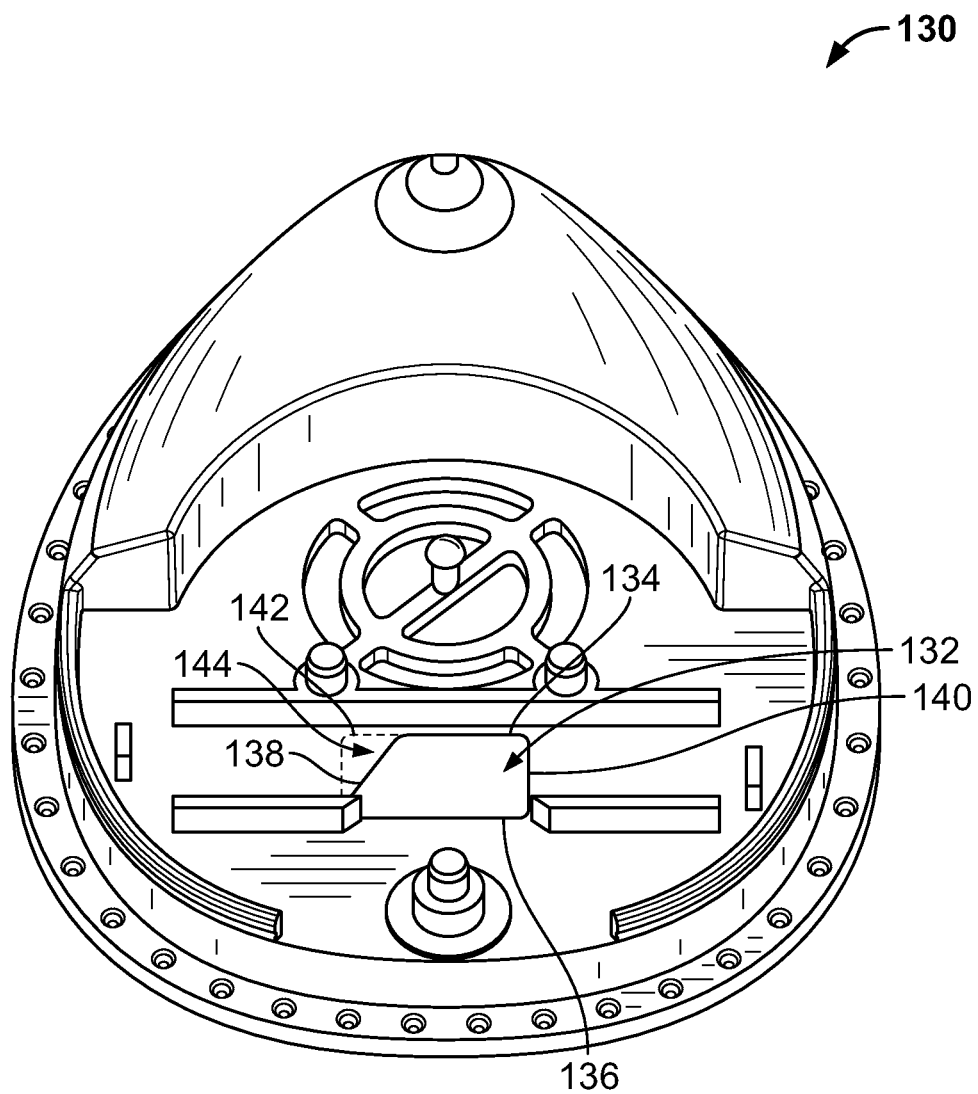
FIG. 4C is a front perspective view of a second embodiment of an insert of the resistance breathing device shown in FIG. 2.

Referring now to FIG. 4C, an alternate embodiment of an insert 130 is shown. In an embodiment, the insert 130 may be substituted in place of the insert 30. The insert 130 is substantially identical to the insert 30 other than insofar as will be described hereinafter. The insert 130 includes an inlet aperture 132 having a shape of a right trapezoid, rather than the rectangular inlet aperture 82 of the insert 30. In an embodiment, the inlet aperture 132 has a shape of a right trapezoid with rounded corners. In an embodiment, an inlet aperture 132 having a shape of a right trapezoid may be formed by truncating a rectangular shape (i.e., the shape of the inlet aperture 82 as described above). FIG. 4C illustrates the insert 130 including the inlet aperture 132. The inlet aperture 132 includes a first side 134 and a second side 136, which are parallel to one another. The first side 134 may be analogous to the first side 88 of the inlet aperture 82, but may be shorter in length as will be described hereinafter. The second side 136 of the inlet aperture 132 may be analogous to the second side 90 of the inlet aperture 82. A diagonal end 138 extends from an end of the second side 136 and forms a forty-five (45) degree angle with the second side 136, ending at the first side 134. A perpendicular end 140 extends from the opposite end of the second side 136 in a perpendicular direction to the first side 134. The perpendicular end 138 may be analogous to the second end 86 of the inlet aperture 82. The outline 142 indicates the profile of the inlet aperture 82 of the insert 30 as superimposed over the inlet aperture 132. It will be apparent to those of skill in the art that the outline 142 is a construct for reference purposes and not a physical element of the insert 130. The area 144 between the inlet aperture 132 and the outline 142 represents the decrease in cross-sectional area of the inlet aperture 132 as compared to the inlet aperture 82 of the insert 30.

Figure 5A:
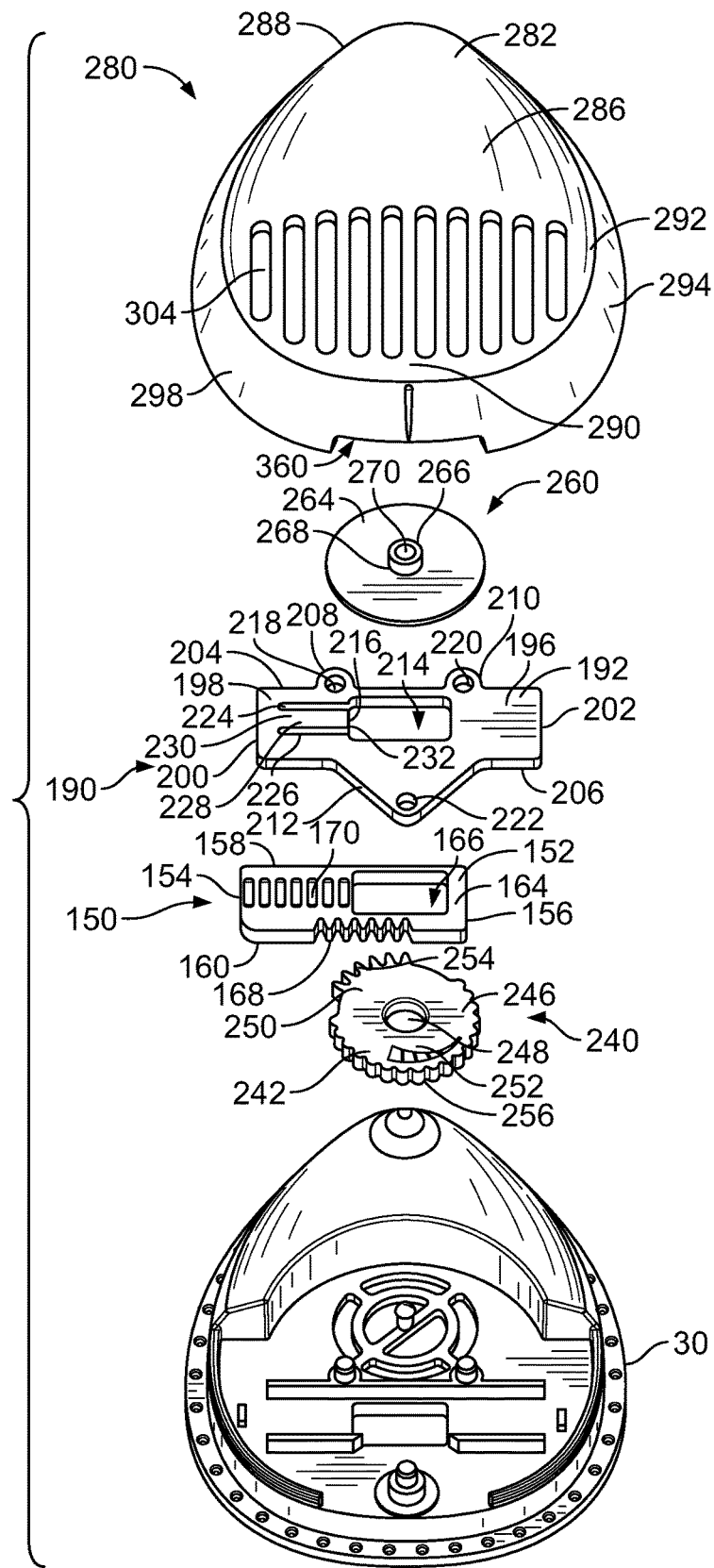
FIG. 5A is an exploded front perspective view of selected elements of the resistance breathing device shown in FIG. 2.
Figure 5B:
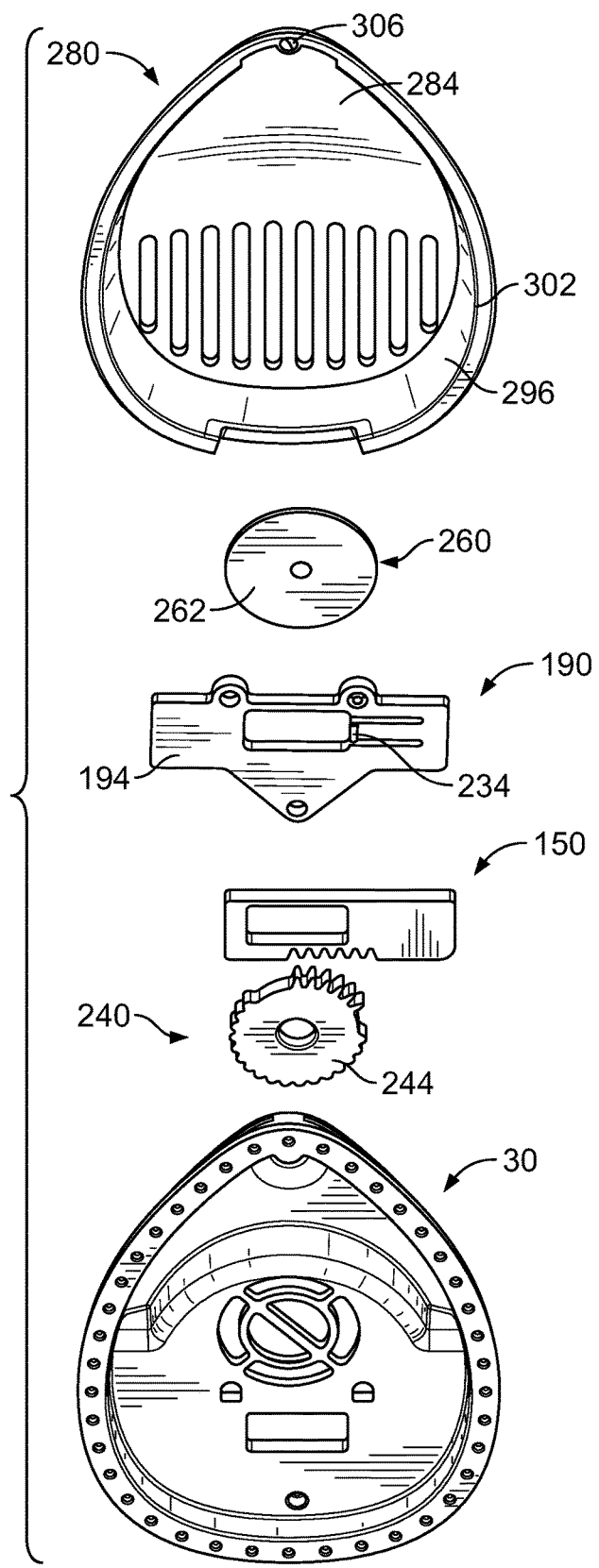
FIG. 5B is an exploded rear perspective view of the elements shown in FIG. 5A.

Referring now to FIGS. 5A and 5B, in an embodiment, the device 10 includes an adjustment slide 150. The adjustment slide 150 includes a substantially rectangular body 152. In an embodiment, the body 152 has rounded corners. In an embodiment, the body 152 has a first end 154, a second end 156 opposite the first end 154, a first side 158, a second side 160 opposite the first side 158, an interior surface 162, and an exterior surface 164 opposite the interior surface 162. In an embodiment, the rectangular body 152 is sized and shaped to be slidably disposed within the rectangle 104 defined by the brackets 92, 94, 96, 100, 102 of the insert 30.

Continuing to refer to FIGS. 5A and 5B, an aperture 166 extends through the body 152 from the interior surface 162 to the exterior surface 164. In an embodiment, the aperture 166 is offset such that it is closer to the second end 156 than to the first end 154. In an embodiment, the aperture 166 has a profile that is substantially identical to that of the inlet aperture 82 of the insert 30. A plurality of teeth 168 is formed in the second side 160 of the body 152. An array of grooves 170 is formed in the exterior surface 164 of the body 152. More particularly, the grooves 170 are located in the portion of the exterior surface 164 located between the aperture 166 and the first end 154. In an embodiment, each of the grooves 170 has a substantially rectangular (e.g., rectangular with rounded corners) profile and a substantially semicircular cross-section. In an embodiment, the adjustment slide 150 includes seven (7) of the grooves 170.

Continuing to refer to FIGS. 5A and 5B, in an embodiment, the rectangular body 152 of the adjustment slide 150 has a height (i.e., as measured from the first side 158 to the second side 160) that is complementary to the height of the rectangle 104 of the insert 30, such that the adjustment slide 150 can be placed within the rectangle 104 and be retained in a desired position with respect to the upper bracket 92 and the lower brackets 94, 96. In an embodiment, the rectangular body 152 has a width (i.e., as measured from the first end 154 to the second end 156) that is less than the width of the rectangle 104 of the insert 30 (i.e., as measured from the first side bracket 100 to the second side bracket 102), such that when the adjustment slide 150 is placed within the rectangle 104, it may be slid along the width of the rectangle 104, as bounded by the side brackets 100, 102. Such motion may be referred to as being along a horizontal (i.e., linear) axis extending parallel to the upper bracket 92 and the lower brackets 94, 96, and perpendicular to the first and second side brackets 100, 102.

Continuing to refer to FIGS. 5A and 5B, the device 10 includes a retainer 190. The retainer 190 has a substantially planar body 192 including an interior surface 194 and an exterior surface 196 opposite the interior surface 194. In an embodiment, the body 192 includes a substantially rectangular main portion 198 having a first end 200, a second end 202 opposite the first end 200, a first side 204, and a second side 206 opposite the first side 204. In an embodiment, first and second semicircular projections 208, 210 extend from the first side 204. In an embodiment, a triangular projection 212 having rounded corners extends from the second side 206. An aperture 214 extends through the body 192 of the retainer 190 in a substantially centered position. More particularly, the aperture 214 is positioned such that, when the retainer 190 is attached to the insert 30 (as will be described in further detail below), the aperture 214 will overlay the inlet aperture 82 of the insert 30. The aperture 214 has a profile that is substantially identical to that of the inlet aperture 82 of the insert 30. The aperture 214 has a first end 216 proximate the first end 200 of the rectangular main portion 198 of the body 192. First, second, and third holes 218, 220, 222 extend through the body 192 of the retainer 190. The first and second hole 218, 220 are positioned within the semicircular projections 208, 210 and are substantially centered therewith, while the third hole 222 is positioned within the triangular projection 212. The holes 218, 220, 222 are each sized and shaped so as to receive a corresponding one of the first, second, and third posts 106, 108, 110 of the insert 30.

Continuing to refer to FIGS. 5A and 5B, in an embodiment, first and second slots 224, 226 extend from the first end 216 of the aperture 214. The first and second slots 224, 226 extend through the body 192 from the interior surface 194 to the exterior surface 196, and extend toward, but do not reach, the first end 200 of the rectangular main portion 198 of the body 192. In an embodiment, the first slot 224 is located proximate the first side 204 of the rectangular main portion 198, while the second slot 226 is located proximate the second side 206 of the rectangular main portion 198. An arm 228 is formed between the first and second slots 224, 226. The arm 228 has a first end 230 proximate the first end 200 of the rectangular main portion 198 and a free second end 232 proximate the aperture 214. A ridge 234 protrudes from the interior surface 194 along the second end 232 of the arm 228. The ridge 234 is sized and shaped so as to selectively engage one of grooves 170 of the adjustment slide 150.

Continuing to refer to FIGS. 5A and 5B, the device 10 includes an adjustment wheel 240. The adjustment wheel 240 includes a substantially circular body 242 having an interior surface 244 and an exterior surface 246 opposite the interior surface 244. A hole 248 extends through the body 242 and is positioned concentrically therewith. The hole 248 is sized and shaped to receive the lower portion 112 of the third post 110 of the insert 30 in a complementary manner, such that the adjustment wheel 240 cannot move across the exterior surface 44 of the inner portion 48 of the insert 30, but can rotate with respect to the insert 30. Such rotation may be described as rotation about a rotational axis extending through the third post 110 and perpendicular to the exterior surface 52 of the inner portion 48 of the insert 30. The rotational axis is perpendicular to and offset from the horizontal axis along which the adjustment slide 150 may move, as described above. The body 242 includes a first side 250 and a second side 252 opposite the first side 250. A plurality of teeth 254 extend from the first side 250 of the body 212, and are sized and shaped so as to mesh with the teeth 168 formed within the body 152 of the adjustment slide 150. A plurality of grips 256 extend from the second side 252 of the body 242, and are sized and shaped so as to enable a user of the device 10 to rotate the adjustment wheel in a manner that will be described in further detail hereinafter. In an embodiment, indicia are printed on the exterior surface 246 of the body 242.

Continuing to refer to FIGS. 5A and 5B, the device 10 includes a flexible, air-impermeable, disc-shaped diaphragm 260. In an embodiment, the diaphragm 260 has an interior surface 262 and an exterior surface 264 opposite the interior surface 262. In an embodiment, a profile of the diaphragm 260 is complementary to that of the exhaust aperture 116 of the insert 30. A tubular post 266 extends from the center 268 of the exterior surface 264. A central opening 270 extends through the diaphragm 260 from the interior surface 262 and through the tubular post 266. In an embodiment, the central opening 270 is sized and shaped to receive the first portion 124 of the stem 122 of the insert 30 so as to enable the diaphragm 260 to be mounted on the insert 30. In an embodiment, the tubular post 266 is formed integrally with the diaphragm 260 and extends generally perpendicularly from the exterior surface 264. In another embodiment, the tubular post 266 is a separate component from the diaphragm 260. In an embodiment, the diaphragm 260 is made of silicone.

Continuing to refer to FIGS. 5A and 5B, in an embodiment, the device 10 includes a face plate 280. The face plate 280 includes an outer plate 282 having an interior surface 284, an exterior surface 286 opposite the interior surface 284, an upper end 288, a lower end 290, and a perimeter 292 defining a profile that is generally similar to that of the insert 30. In an embodiment, the outer plate 282 is substantially planar. In an embodiment, the outer plate 282 is curved such that the interior surface 284 is concave and the exterior surface 286 is convex. A perimeter plate 294 extends from the perimeter 292 and away from the interior surface 284 of the outer plate 282 by a first distance. The perimeter plate 294 has an interior surface 296 and an exterior surface 298 opposite the interior surface 296. The perimeter plate 294 further includes a gap 300 proximate the lower end 290 of the outer plate 282, within which the perimeter plate 294 extends away from the interior surface 284 of the outer plate 282 by a second distance that is less than the first distance.

In an embodiment, a ridge 302 extends from the interior surface 296 of the perimeter plate 294. In an embodiment, the ridge 302 extends around the entirety of the perimeter plate 294 at a location distal to the outer plate 282. In an embodiment, the ridge 302 is sized, shaped, and positioned so as to engage the groove 80 of the insert 30, and thereby retain the face plate 280 and the insert 30 in proximity to one another. In an embodiment, slots 304 extend through the outer plate 282 from the interior surface 284 to the exterior surface 286 thereof. In an embodiment, the slots 304 are positioned proximate the lower end 290 of the outer plate 282. In an embodiment, the face plate 280 is contoured to provide an aesthetically pleasing appearance to the device 10. In an embodiment, the slots 304 are sized and shaped so as to hide the internal elements of the device 10 (i.e., the insert 30, the adjustment slide 150, the retainer 190, the adjustment wheel 240, and the diaphragm 260) from view.

In an embodiment, the insert 30 (or, alternatively, the insert 130), the adjustment slide 150, the retainer 190, the adjustment wheel 240, and the face plate 280 are made from a polycarbonate ("PC") plastic. In an embodiment, the insert 30 (or, alternatively, the insert 130), the adjustment slide 150, the retainer 190, the adjustment wheel 240, and the face plate 280 are made from a nylon plastic. In an embodiment, the insert 30 (or, alternatively, the insert 130), the adjustment slide 150, the retainer 190, the adjustment wheel 240, and the face plate 280 are made from a polypropylene plastic. In an embodiment, the insert 30 (or, alternatively, the insert 130), the adjustment slide 150, the retainer 190, the adjustment wheel 240, and the face plate 280 are made from another material selected such that they are capable of use as described herein. In an embodiment each of the insert 30 (or, alternatively, the insert 130), the adjustment slide 150, the retainer 190, the adjustment wheel 240, and the face plate 280 is made a material that is different from one another. In an embodiment, at least one of the insert 30, the adjustment slide 150, the retainer 190, the adjustment wheel 240, and the face plate 280 is made from a translucent material. In an embodiment, at least one of the insert 30 (or, alternatively, the insert 130), the adjustment slide 150, the retainer 190, the adjustment wheel 240, and the face plate 280 is made from an opaque material.

Referring back to FIGS. 2 and 3, in an embodiment, the outer layer 12 includes straps 310, 312 extending in opposite directions away from a central portion 314. In an embodiment, the central portion 314 includes an aperture 316 that is sized and shaped to surround the face mask 14 and retain the face mask 14 therein, as will be described in further detail below with reference to assembly of the device 10. In an embodiment, the outer layer 12 is made from a fabric material. In an embodiment, the outer layer 12 is made from an elastic material. In an embodiment, the size of the outer layer 12 is adjustable (e.g., the lengths of the straps 310, 312 are adjustable). In an embodiment, the straps 310, 312 include corresponding ends 318, 320. In an embodiment, the ends 318, 320 of the straps 310, 312 incorporate corresponding hook and loop fasteners 322, 324 to enable the ends 318, 320 to be secured to one another, thereby to enable the device 10 to be affixed about the user's head (see, e.g., FIG. 1). In other embodiments, the ends 318, 320 of the straps 310, 312 include other securing means known in the art, such as clips, press-fit snaps, buttons, or the like. In an embodiment, the straps 310, 312 include cutouts 326, 328 for seating around the user's ears to further secure the device 10 to the user's face.

Referring now to FIGS. 5A through 6C, assembly of the device 10 is described. The disclosure herein will refer to a device 10 including the insert 30 shown in FIGS. 4A and 4B, but it will be apparent to those of skill in the art that the insert 130 shown in FIG. 4C may be substituted for the insert 30. In an embodiment, the face mask 14 and the insert 30 are integrally formed with one another by an overmolding process. When the face mask 14 and the insert 30 are so formed, the entire periphery of the outer portion 40 of the insert 30 is disposed within the groove 26 of the lip 24 of the face mask 14, and the material of the face mask 14 extends through each of the perforations 46 that are formed in the outer portion 40 of the insert 30. The elastic nature of the face mask 14, coupled with the overmolding as described above, retains the insert 30 within the aperture 22 (and, more particularly, within the groove 26) in an engagement that is air-tight and structurally secure. However, for clarity of illustration, the face mask 14 is not shown in FIGS. 4A-5C.

Continuing to refer to FIGS. 5A through 6C, the adjustment slide 150 is placed within the rectangle 104 of the insert 30 such that the interior surface 162 of the body 152 of the adjustment slide 150 faces the exterior surface 52 of the inner portion 48 of the insert 30. The position of the adjustment slide 150 is bounded by the brackets 92, 94, 96, 100, 102 of the insert 30. The grooves 170 of the exterior surface 164 of the body 152 of the adjustment slide 150 face away from the insert 30.

Continuing to refer to FIGS. 5A through 6C, the adjustment wheel 240 is placed over the third post 110 of the insert 30, such that the lower portion 112 of the third post 110 is received within the hole 248 of the adjustment wheel 240, and such that the interior surface 244 of the body 242 of the adjustment wheel 240 faces the exterior surface 52 of the inner portion 48 of the insert 30. When the adjustment wheel 240 is so positioned, the first side 250 of the adjustment wheel 240 extends through the space 98 between the first and second lower brackets 94, 96 of the insert 30, allowing the teeth 254 of the adjustment wheel 240 to mesh with the teeth 168 of the adjustment slide 150. Also, when the adjustment wheel 240 is so positioned, the second side 252 of the adjustment wheel 240 extends through the space 78 between the first and second perimeter portions 74, 76 of the insert 30, allowing the grips 256 of the adjustment wheel to extend past the lower end 34 of the insert 30. As described above with reference to the adjustment wheel 240, the adjustment wheel 240 is able to rotate about the third post 110, but cannot move across the exterior surface 52.

Continuing to refer to FIGS. 5A through 6C, the retainer 190 is placed over the assembled combination of the insert 30, the adjustment slide 150, and the adjustment wheel 240. Each of the first, second, and third holes 216, 218, 220 of the retainer 190 receives a corresponding one of the first, second, and third posts 106, 108, 110 of the insert 30. The interior surface 194 of the body 192 of the retainer 190 abuts the exterior surface 164 of the body 152 of the adjustment slide 150, the exterior surface 246 of the body 242 of the adjustment wheel 240, and the brackets 92, 94, 96, 100, 102 of the insert 30. The ridge 234 at the second end 232 of the arm 228 of the retainer 190 is received by one of the grooves 170 of the adjustment slide 150. The retainer 190 is secured in place by a process involving the use of heat staking or sonic welding to secure the first, second, and third posts 106, 108, 110 of the insert 30 within the corresponding ones of the first, second, and third holes 216, 218, 220 of the retainer 190. As a result of such a process, joints 340 (see FIGS. 6A through 6C) are formed and fix the first, second, and third posts 106, 108, 110 of the insert 30 within the corresponding ones of the first, second, and third holes 216, 218, 220. When the retainer 190 is secured in this manner, the adjustment slide 150 and the adjustment wheel 240 are held in position by the retainer 190 such that they cannot move away from the insert 30. More particularly, the joints 340 maintains the retainer 190, the adjustment slide 150, and the insert 30 in sufficiently close alignment to one another such that they form a substantially airtight seal with one another. Consequently, air cannot pass around the adjustment slide 150 and through the inlet aperture 82 of the retainer 30.

Continuing to refer to FIGS. 5A through 6C, the diaphragm 260 is engaged with the insert 30 by inserting the stem 122 of the insert 30 through the opening 270 within the post 266 of the diaphragm 260, such that the interior surface 262 of the diaphragm 260 abuts the biasing element 118 of the insert 30. When the diaphragm 260 is so positioned, the first portion 124 of the stem 122 is within the opening 270 of the diaphragm, while the larger second portion 126 of the stem 12 abuts the post 266 of the diaphragm 260. Consequently, once the diaphragm 260 is engaged with the stem 122, the abutment of the second portion 126 of the stem 122 and the post 266 of the diaphragm 260 holds the interior surface 262 of the diaphragm 260 to the biasing element 118 of the insert 30 and prevents removal of the diaphragm 260 from the insert 30.

Continuing to refer to FIGS. 5A through 6C, the face plate 280 is engaged to the insert 30 by engaging the ridge 302 of the face plate 280 to the groove 80 of the insert 30. During such engagement, the projection 306 of the face plate 280 may be aligned with the indentation 66 in the exterior surface 64 of the seating portion 60 of the insert 30 to facilitate proper alignment of the face plate 280 with the insert 30. The face plate 280 may be permanently fixed to the insert 30 (e.g., through the use of the joints 340 described above with reference to FIGS. 6A through 6C), or may be removable therefrom.

As noted above, in an embodiment, the insert 30 and the face mask 14 are overmolded and integrally formed with one another. In another embodiment, the insert 30 and the face mask 14 may be separately formed and subsequently engaged with one another. In such an embodiment, the assembled combination of the insert 30, the adjustment slide 150, the adjustment wheel 240, the retainer 190, the diaphragm 260, and the face plate 280 is engaged with the face mask 14 by placing the insert 30 within the aperture 22 of the face mask 14 and positioning the entire periphery of the outer portion 40 of the insert 30 within the groove 26 of the lip 24 of the face mask 14, in which position the face mask 14 forms an air-tight seal around the insert 30. An adhesive or a sealant may be placed within the groove 26 to attain a secure and permanent seal around the insert 30. In another embodiment including a separately formed insert 30 and face mask 14, the insert 30 and the face mask 14 may be engaged with one another, as described above, prior to engaging the remaining elements of the device 10 with the insert 30.

Referring now to FIGS. 2-3, the outer layer 12 is laid over the face mask 14, which has the assembled combination of the insert 30, the adjustment slide 150, the adjustment wheel 240, the retainer 190, the diaphragm 260, and the face plate 280 retained therein. The aperture 316 of the outer layer 12 is stretched and pulled over the assembled combination of the insert 30, the adjustment slide 150, the adjustment wheel 240, the retainer 190, the diaphragm 260, and the face plate 280 until the outer layer 12 abuts the face mask 14. The outer layer 12 is then allowed to return to its relaxed (i.e., unstretched) size such that the aperture 316 constricts around the exterior surface 58 of the first transition portion 54 of the insert 30, and is held between the face mask 14 and the perimeter plate 294 of the face plate 280. Consequently, the outer layer 12 retains the remaining elements of the device 10 in the aperture 316.

Referring now to FIGS. 1 and 6A through 6C, use of the exemplary device 10 by a user according to an exemplary embodiment will now be described. Initially, the device 10 is affixed to the users face by placing the face mask 14 over the user's mouth and nose, passing the straps 310, 312 around either side of the user's head such that the cutouts 326, 328 overlap the user's ears, and securing the ends 318, 320 to one another using the hook and loop fasteners 322, 324. The user may adjust the hook and loop fasteners 322, 324 to ensure that the face mask 14 is pulled against the user's face with sufficient force such that the perimeter 16 thereof is pressed tightly against the user's face and around the user's mouth and nose. By such action, an airtight seal is created between the user's face and the face mask 14, thereby ensuring that air can only pass in, and out for the user's inhalation and exhalation through the various apertures formed within the insert 30.

Figure 6A:
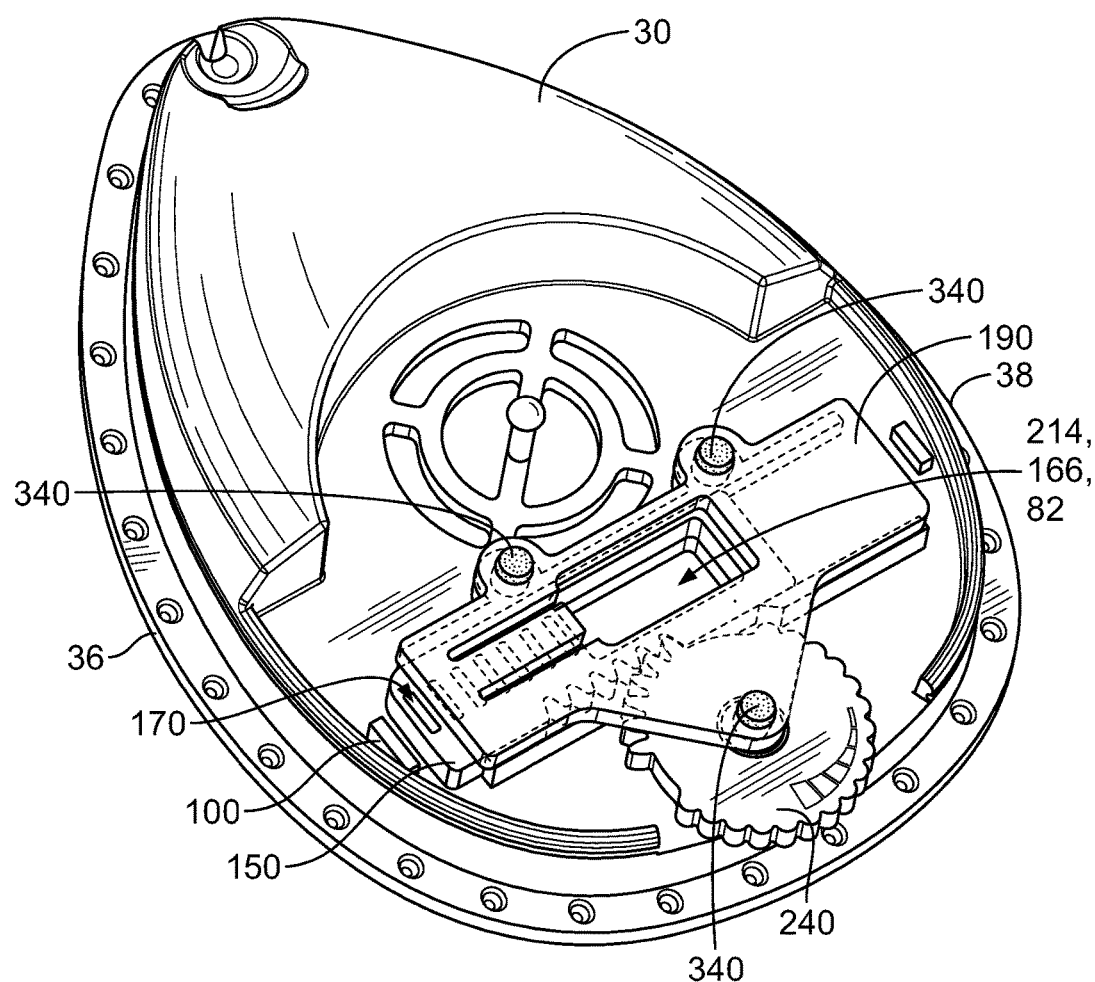
FIG. 6A is an assembled front perspective view of some of the elements shown in FIG. 5A, said elements being configured in a first position.
Figure 6B:
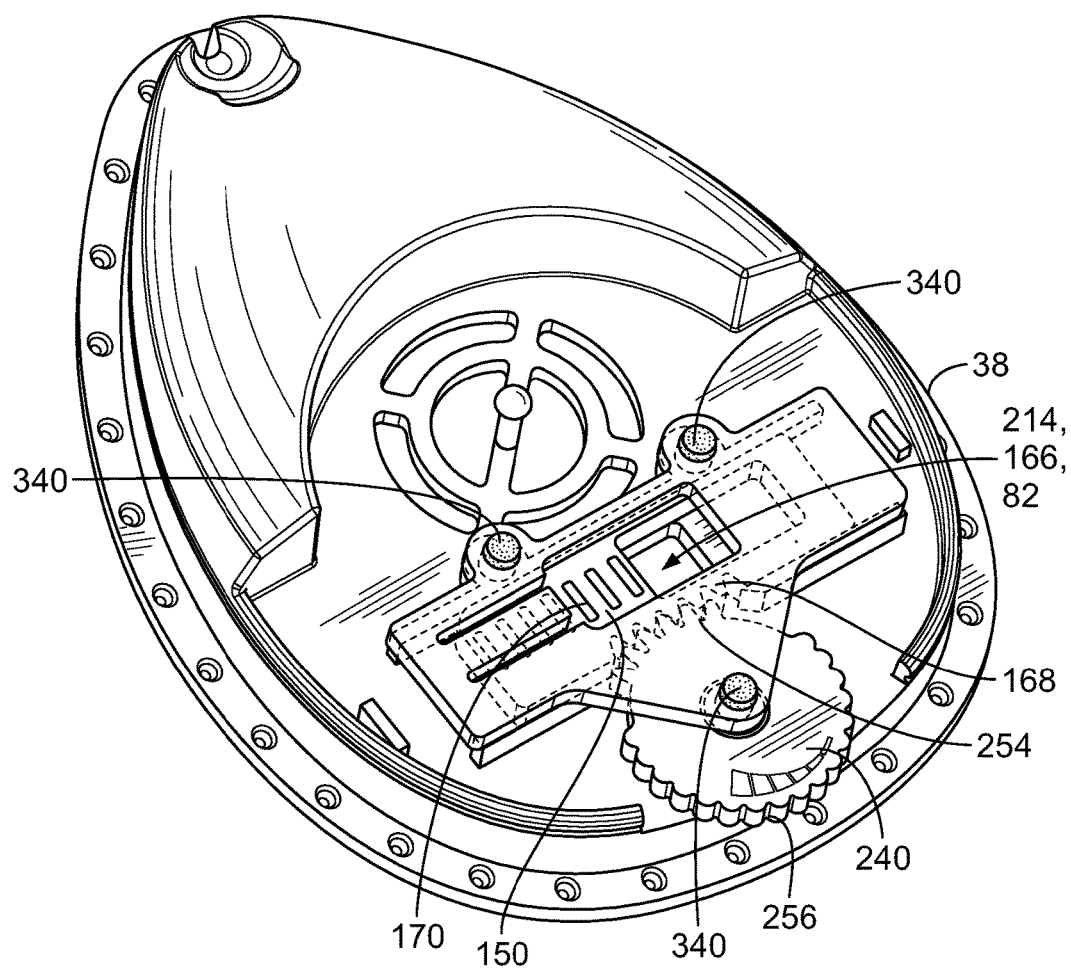
FIG. 6B is an assembled front perspective view of the elements shown in FIG. 6A, said elements being configured in a second position.
Figure 6C:
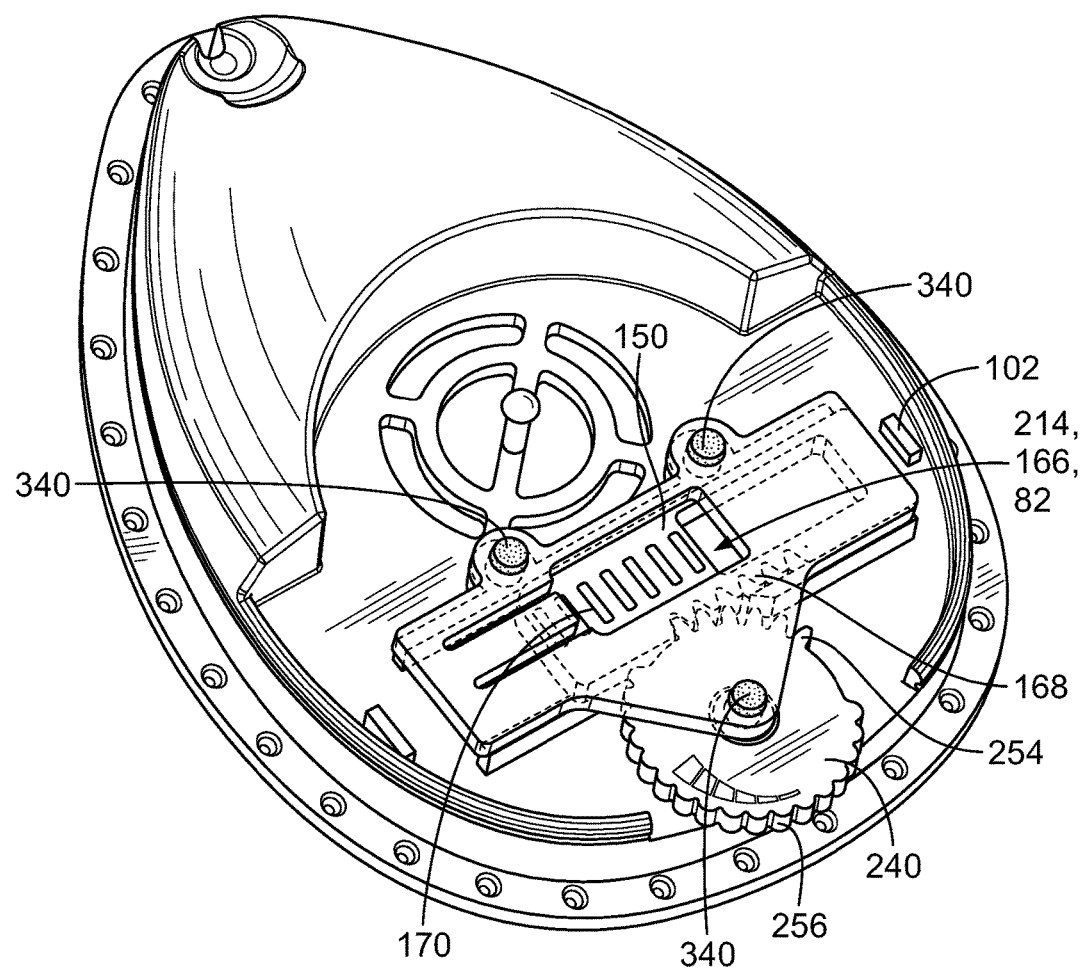
FIG. 6C is an assembled front perspective view of the elements shown in FIG. 6A, said elements being configured in a third position.

Referring now to FIGS. 6A through 6C, adjustment of the exemplary device 10 by a user will now be described. More particularly, FIGS. 6A, 6B, and 6C illustrate certain elements of the device 10 (i.e., the insert 30, the adjustment slide 150, the adjustment wheel 240, and the retainer 190) with remaining elements of the device 10 (including, most relevant, the face plate 280) omitted for clarity. FIG. 6A shows a first position of the adjustment slide 150 with respect to the insert 30. Specifically, the adjustment slide 150 is positioned so as to abut the first side bracket 100, as far toward the first lateral side 36 of the insert 30 as the adjustment slide 150 may travel within the rectangle 104 of the insert 30. When the adjustment slide 150 is so positioned, the ridge 234 of the arm 228 of the retainer 190 rests within the one of the grooves 170 of the adjustment slide 150 that is closest to the aperture 166 of the adjustment slide 150. Also, when the adjustment slide 150 is so positioned, the entirety of the aperture 166 of the adjustment slide 150 overlaps corresponding entireties of the inlet aperture 82 of the insert 30 and the aperture 214 of the retainer 190 (i.e., which are aligned with one another because of the fixed position of the retainer 190 with respect to the insert 30). Consequently, a comparatively large volume of air may pass through the aligned combination of the aperture 214 of the retainer 190, the aperture 166 of the adjustment slide 150, and the inlet aperture 82 of the insert 30.

Referring now to FIG. 6B, in some circumstances, the user may wish to decrease the volume of air that may pass into the face mask 14. In this case, the user may manipulate the adjustment wheel 240, with the grips 256 aiding the user's ability to do so, and may rotate the adjustment wheel 240 in a clockwise direction as viewed from the perspective shown in FIGS. 6A through 6C. Such rotation of the adjustment wheel 240 and, consequently, the teeth 254 thereof drives corresponding motion of the teeth 168 of the adjustment slide 150, thereby causing the adjustment slide 150 to move toward the second lateral side 38 of the insert 30. As the adjustment slide 150 moves toward the second lateral side 38 of the insert 30, a smaller portion of the aperture 166 of the adjustment slide 150 will overlap corresponding smaller portions of the inlet aperture 82 of the insert 30 and the aperture 214 of the retainer 190. Consequently, a correspondingly smaller volume of air will be able to pass through the aligned combination of the aperture 214 of the retainer 190, the aperture 166 of the adjustment slide 150, and the inlet aperture 82 of the insert 30. Referring now to FIG. 6B, the adjustment slide 150 is shown in an intermediate position in which the ridge 234 of the arm 228 of the retainer 190 rests within an intermediate one of the grooves 170 of the adjustment slide and an intermediate portion of the aperture 166 of the adjustment slide 150 overlaps intermediate portions of the inlet aperture 82 of the insert 30 and the aperture 214 of the retainer 190.

Referring now to FIG. 6C, if the user wishes to allow an even smaller degree of air flow into the face mask 14, the user may continue to rotate the adjustment wheel 240 until the adjustment slide 150 has been driven to such an extent that it has traveled as far as possible toward the second lateral side 38 of the insert 30, and abuts the second side bracket 102 of the insert 30. When the adjustment slide 150 is so positioned, the ridge 234 of the arm 228 of the retainer 190 rests within the one of the grooves 170 of the adjustment slide 150 that is closest to the first end 154 of the body 152 of the adjustment slide 150. Also, when the adjustment slide 150 is so positioned, only a very small portion of the aperture 166 of the adjustment slide 150 overlaps corresponding very small portions of the inlet aperture 82 of the insert 30 and the aperture 214 of the retainer 190 (i.e., which remain aligned with one another because of the fixed position of the retainer 190 with respect to the insert 30). Consequently, a smaller volume of air may pass through the aligned combination of the aperture 214 of the retainer 190, the aperture 166 of the adjustment slide 150, and the inlet aperture 82 of the insert 30.

Referring now to FIGS. 1 through 6C, when the user inhales, a reduced air pressure is induced within the face mask 14 as compared to the surrounding atmosphere. This reduced air pressure urges the diaphragm 260 against the biasing element 118, in which position the diaphragm 260 completely overlaps and seals the exhaust aperture 116 of the insert 30. Due to such sealing, air cannot pass from the user's surroundings to within the face mask 14 through exhaust aperture 116 of the insert 30. As a result, the only air that can pass from the user's surroundings to within the face mask 14 is air allowed to pass through the aligned combination of the aperture 214 of the retainer 190, the aperture 166 of the adjustment slide 150, and the inlet aperture 82 of the insert 30. As described above, the user of the device 10 may configure the size of the portion of the aperture 166 of the adjustment slide 150 that overlaps the aperture 214 of the retainer 190 and the inlet aperture 82 of the insert 30 by adjusting the position of the adjustment wheel 240 to drive corresponding motion of the adjustment slide 150 with respect to the insert 30. Therefore, by adjusting the position of the adjustment wheel 240, the user of the device 10 may control the amount of air that the device 10 allows him or her to inhale.

As discussed above, the insert 130 having the trapezoidal inlet aperture 132 may be used in place of the insert 30 having the rectangular inlet aperture 82. In such an embodiment, the amount of air that is allowed pass through the aligned combination of the aperture 214 of the retainer 190, the aperture 166 of the adjustment slide 150, and the inlet aperture 132 of the insert 30, when the device is positioned as shown in FIG. 6A, will be less than that described above with reference to FIG. 6A, due to the reduced area of the inlet aperture 132 of the insert 130 as compared to the inlet aperture 82 of the insert 30 (i.e., as represented by the area 144 shown in FIG. 4C). Therefore, an embodiment of a resistance breathing device including the insert 130 may provide a greater degree of inhalation resistance, when configured to allow the maximum allowable amount of air to be inhaled therethrough, than the device 10 including the insert 30.

Continuing to refer to FIGS. 1 through 6C, when the user exhales, an increased air pressure is induced within the face mask 14 as compared to the surrounding atmosphere. This increased air pressure urges the diaphragm 260 away from the biasing element 118 of the insert 30, in which position the diaphragm 260 does not seal the exhaust aperture 116 of the insert 30. Due to such lack of sealing, exhaled air can freely pass from within the face mask 14 to the user's surroundings through the exhaust aperture 116 of the insert 30 and the slots 304 of the face plate 280. Because the combination of the diaphragm 260, the biasing element 118, and the exhaust aperture 116 cooperate to allow the user exhale freely therethrough, while preventing air inhalation therethrough, this combination of elements may be considered to form an air exhaust valve assembly.

The resistance breathing device 10 restricts the volume of air that can be inhaled by a user during ventilation to the volume of air that can pass through the portions of the aperture 166 of the adjustment slide 150 that overlaps the aligned combination of the aperture 214 of the retainer 190 and the inlet aperture 82 of the insert 30. Consequently, the resistance breathing device 10 restricts the oxygen available to the user's body when the device 10 is worn by the user. Users who wear the resistance breathing device 10 during physical training may realize improved benefits from such physical training due to such restriction. Moreover, because the user may select the position of the adjustment slide 150 as described above, and thereby select the sizes of the portions of the aperture 166 of the adjustment slide 150 that overlaps the aligned combination of the aperture 214 of the retainer 190 and the inlet aperture 82 of the insert 30, the user may select the degree of restriction of inhalation of oxygen to be provided by the resistance breathing device 10.

Depending upon the position of the adjustment slide 150 with respect to the insert 30, and with respect to the retainer 190 that is fixed to the insert 30, the ridge 234 of the arm 228 of the retainer 190 either will be within one of the grooves 170 of the adjustment slide 150 or will be abutting a portion of the exterior surface 164 of the adjustment slide 150 that is between two of the grooves 170. When the ridge 234 is positioned within one of the grooves 170, a comparatively large amount of force will be required to cause lateral motion of the adjustment slide 150 with respect to the insert 30, because the applied force must also drive the ridge 234, and, consequently, the arm 228 of the retainer 190, upward (i.e., away from the adjustment slide 150 and the insert 30) in order for such lateral motion to be permitted. Conversely, when the ridge 234 is positioned between two of the grooves 170, the arm 228 is already flexed away from the adjustment slide 150 and the insert 30, and a comparatively small amount of force will be required to cause lateral motion of the adjustment slide 150 with respect to the insert 30. Consequently, the position of the adjustment slide 150 and the corresponding position of the adjustment wheel 240 will feel "settled" to the user when the ridge 234 is within one of the grooves 170, and will feel "unsettled" to the user when the ridge 234 is not within one of the grooves 170. This tactile sensation may serve as a guide to the user of the device 10 in adjusting the position of the adjustment wheel 240, particularly when the device 10 has already been fastened about the user's head and cannot readily be seen by the user.

As a further result of the above, each of the grooves 170 may provide a discrete position setting for the adjustment slide 150 and the adjustment wheel 240, each of which corresponds to a different degree of overlap of the aperture 166 of the adjustment slide 150 with the inlet aperture 82 of the insert 30 and the aperture 214 of the retainer 190, and each of which, in turn, corresponds to a volume of air that may pass through the aligned combination of the aperture 214 of the retainer 190, the aperture 166 of the adjustment slide 150, and the inlet aperture 82 of the insert 30. Consequently, the user may more easily configure the device 10 to allow a desired degree of air flow into the face mask 14 (e.g., the same degree as used in a previous workout; a greater restriction of air flow into the face mask 14 than a previous workout) through tactile sensation alone, without the need to remove the device 10 for visual inspection.

It will be understood that the embodiments described herein are merely exemplary and that a person skilled in the art may make many variations and modifications without departing from the spirit and scope of the invention. All such variations and modifications are intended to be included within the scope of the invention, as embodied in the appended claims presented.

What is claimed is:

1. A resistance breathing device, comprising:
   a face mask having an interior surface, an exterior surface opposite said interior surface, an aperture extending through said face mask from said exterior surface to said interior surface, and a perimeter, wherein said face mask is adapted to overlay a user's mouth and nose such that said perimeter forms an air-tight seal with the user's face and around the user's mouth and nose and said face mask defines an internal area between said interior surface of said face mask and the user's face;
   an outer layer overlaying said face mask and having a pair of straps with inter-engaging ends for affixing said face mask about the user's face;
   an insert having an interior surface, an exterior surface opposite said interior surface of said insert, and at least one inlet aperture extending therethrough, said insert being positioned within said aperture of said face mask;
   an adjustment slide including an interior surface, an exterior surface opposite said interior surface of said adjustment slide, and at least one inlet aperture extending therethrough, said adjustment slide being positioned adjacent to said insert such that said interior surface of said adjustment slide abuts said exterior surface of said insert, said adjustment slide being movable linearly along a linear axis with respect to said insert between a first position and a second position, wherein when said adjustment slide is in its said first position, a first portion of said at least one inlet aperture of said adjustment slide overlays a first portion of said at least one inlet aperture of said insert, and wherein when said adjustment slide is in its said second position, a second portion of said at least one inlet aperture of said adjustment slide overlays a second portion of said at least one inlet aperture of said insert, said second portion of said at least one inlet aperture of said adjustment slide being larger in size than said first portion of said at least one inlet aperture of said adjustment slide;
   an adjustment wheel attached movably to said insert such that said adjustment wheel is movable rotatably with respect to said insert between a first position and a second position, said first position of said adjustment wheel corresponding to said first position of said adjustment slide, said second position of said adjustment wheel corresponding to said second position of said adjustment slide, whereby when said adjustment wheel is moved between its said first position and its said second position, said adjustment slide is moved between its said first position and its said second position; and an air exhaust valve assembly adapted to prevent air from passing therethrough from an external environment to said internal area of said face mask, said air exhaust valve assembly being adapted to allow air to pass therethrough from said internal area of said face mask to the external environment.

2. The resistance breathing device of claim 1, wherein said adjustment slide includes a first plurality of teeth, and wherein said adjustment wheel includes a second plurality of teeth, wherein said adjustment slide and said adjustment wheel are positioned adjacent one another such that said first plurality of teeth of said adjustment slide mesh with said second plurality of teeth of said adjustment wheel.

3. The resistance breathing device of claim 2, wherein said adjustment wheel rotates about a rotational axis to move between its said first position and its said second position, said rotational axis being perpendicular to said linear axis.

4. The resistance breathing device of claim 1, further comprising a retainer having an interior surface, an exterior surface opposite said interior surface of said retainer, and at least one inlet aperture, said retainer overlaying said adjustment slide such that said interior surface of said retainer abuts said exterior surface of said adjustment slide so as to maintain said adjustment slide in its position adjacent said insert and such that said at least one inlet aperture of said retainer overlays said at least one inlet aperture of said insert.

5. The resistance breathing device of claim 4, wherein said adjustment slide includes a plurality of grooves formed in said exterior surface of said adjustment slide and spaced along said linear axis, wherein said retainer includes a ridge projecting from said interior surface of said retainer, wherein said ridge of said retainer is positioned within a first one of said plurality of grooves of said adjustment slide when said adjustment slide is in its said first position, and wherein said ridge of said retainer is positioned within a second one of said plurality of grooves of said adjustment slide when said adjustment slide is in its said second position.

6. The resistance breathing device of claim 5, wherein said ridge of said retainer is positioned adjacent to said at least one inlet aperture of said retainer.

7. The resistance breathing device of claim 5, wherein said ridge of said retainer and said plurality of grooves of said adjustment slide are sized and shaped such that when said ridge is positioned within one of said plurality of grooves, said ridge and said one of said plurality of grooves cooperate to resist movement of said adjustment slide along said linear axis.

8. The resistance breathing device of claim 4, wherein said at least one inlet aperture of said retainer is substantially rectangular in shape.

9. The resistance breathing device of claim 1, wherein said at least one inlet aperture of said adjustment slide is substantially rectangular in shape.

10. The resistance breathing device of claim 9, wherein said at least one inlet aperture of said adjustment slide has rounded corners.

11. The resistance breathing device of claim 9, wherein said at least one inlet aperture of said insert is substantially rectangular in shape.

12. The resistance breathing device of claim 11, wherein a size of said at least one inlet aperture of said adjustment slide is equal to a size of said at least one inlet aperture of said insert.

13. The resistance breathing device of claim 9, wherein said at least one inlet aperture of said insert is right trapezoidal in shape.

14. The resistance breathing device of claim 13, wherein said right trapezoidal shape includes rounded corners.

15. The resistance breathing device of claim 13, wherein said at least one inlet aperture of said insert is smaller than said at least one inlet aperture of said adjustment slide.

16. The resistance breathing device of claim 1, wherein said insert includes a first lateral side, a second lateral side opposite said first lateral side, a first side bracket extending from said exterior surface of said insert proximate said first lateral side, and a second side bracket extending from said exterior surface of said insert proximate said second lateral side, said first and second side brackets cooperating to define an allowable range of travel of said adjustment slide along said linear axis.

17. The resistance breathing device of claim 1, further comprising a face plate having an interior surface and an exterior surface opposite said interior surface of said face plate, said face plate overlaying said insert and being oriented such that said interior surface of said face plate faces said insert.

18. The resistance breathing device of claim 1, wherein said face mask is overmolded to said insert.

19. The resistance breathing device of claim 1, wherein said insert includes at least one outlet aperture positioned offset from said at least one inlet aperture of said insert, each of said at least one outlet aperture including a biasing member extending across said one of at least one outlet aperture of said insert and a stem extending from a center of said biasing member and away from said insert, said stem including a first portion adjacent said center of said biasing member and a second portion opposite said first portion of said stem, said first portion of said stem having a first diameter, and said second portion of said stem having a second diameter that is larger than said first diameter.

20. The resistance breathing device of claim 19, wherein said air exhaust valve assembly includes said at least one outlet aperture of said insert and at least one flexible membrane having a first side, a second side opposite said first side, a profile complementary to said at least one outlet aperture of said insert, a post extending from said first side, and a central hole extending through said post and said first and second sides and sized and shaped to receive said first portion of said stem of said insert, said at least one flexible membrane being disposed adjacent said insert such that said first portion of said stem of each of said at least one outlet aperture of said insert is disposed within said central hole of a corresponding one of said at least one flexible membrane, such that said second side of each of said at least one flexible membrane abuts said biasing member of said corresponding one of at least one outlet aperture of said insert, and such that said second portion of said stem of each of said at least one outlet aperture abuts said post of said corresponding one of said at least one flexible membrane so as to retain said at least one flexible membrane adjacent to said insert.

\* \* \* \* \*

UNITED STATES PATENT AND TRADEMARK OFFICE
CERTIFICATE OF CORRECTION

| | | |
|---|---|---|
| PATENT NO. | : 9,643,048 B1 | |
| APPLICATION NO. | : 15/297911 | |
| DATED | : May 9, 2017 | |
| INVENTOR(S) | : Casey Danford | |

It is certified that error appears in the above-identified patent and that said Letters Patent is hereby corrected as shown below:

In the Specification

Column 4, Line 16, delete "1-5C" and insert --1-6C--.

Column 11, Line 16, delete "4A-5C" and insert --4A-6C--.

Signed and Sealed this
Eighth Day of August, 2017

Joseph Matal
*Performing the Functions and Duties of the*
*Under Secretary of Commerce for Intellectual Property and*
*Director of the United States Patent and Trademark Office*